(12) United States Patent
Pusic et al.

(10) Patent No.: US 11,369,634 B2
(45) Date of Patent: *Jun. 28, 2022

(54) EXOSOME-BASED THERAPEUTICS AGAINST NEURODEGENERATIVE DISORDERS

(71) Applicant: The University of Chicago, Chicago, IL (US)

(72) Inventors: Kae M. Pusic, Chicago, IL (US); Yelena Y. Grinberg, Chicago, IL (US); Richard P. Kraig, Chicago, IL (US); Aya D. Pusic, Chicago, IL (US)

(73) Assignee: The University of Chicago, Chicago, IL (US)

( * ) Notice: Subject to any disclaimer, the term of this patent is extended or adjusted under 35 U.S.C. 154(b) by 681 days.

This patent is subject to a terminal disclaimer.

(21) Appl. No.: 16/259,563

(22) Filed: Jan. 28, 2019

(65) Prior Publication Data

US 2019/0160097 A1 May 30, 2019

Related U.S. Application Data

(63) Continuation of application No. 14/420,680, filed as application No. PCT/US2013/055187 on Aug. 15, 2013, now Pat. No. 10,231,997.

(60) Provisional application No. 61/683,596, filed on Aug. 15, 2012.

(51) Int. Cl.

| | |
|---|---|
| *A61K 35/15* | (2015.01) |
| *C12N 15/88* | (2006.01) |
| *A61K 9/50* | (2006.01) |
| *A61K 35/30* | (2015.01) |
| *A61K 35/35* | (2015.01) |
| *C12N 15/11* | (2006.01) |
| *A61K 31/7088* | (2006.01) |
| *A61K 48/00* | (2006.01) |
| *C12N 5/079* | (2010.01) |
| *C12N 15/113* | (2010.01) |

(52) U.S. Cl.
CPC .......... *A61K 35/15* (2013.01); *A61K 9/5068* (2013.01); *A61K 31/7088* (2013.01); *A61K 35/30* (2013.01); *A61K 35/35* (2013.01); *A61K 48/00* (2013.01); *C12N 5/0618* (2013.01); *C12N 15/111* (2013.01); *C12N 15/113* (2013.01); *C12N 15/88* (2013.01); *C12N 2310/14* (2013.01); *C12N 2310/141* (2013.01); *C12N 2320/31* (2013.01); *C12N 2320/32* (2013.01)

(58) Field of Classification Search
CPC .. A61K 31/7088; A61K 35/30; C12N 5/0618; C12N 15/111; C12N 15/113; C12N 15/88; C12N 2310/14; C12N 2310/141
See application file for complete search history.

(56) References Cited

U.S. PATENT DOCUMENTS

| | | | |
|---|---|---|---|
| 7,709,616 B2 | 5/2010 | Bentwich et al. | |
| 10,231,997 B2* | 3/2019 | Pusic | .............. A61P 25/06 |
| 2006/0068405 A1 | 3/2006 | Diber et al. | |
| 2010/0151480 A1 | 6/2010 | Taylor et al. | |
| 2011/0003008 A1 | 1/2011 | Lim | |
| 2011/0191874 A1 | 8/2011 | Carlock et al. | |

FOREIGN PATENT DOCUMENTS

| | | |
|---|---|---|
| WO | WO 99/03499 | 1/1999 |
| WO | WO 00/44389 | 8/2000 |
| WO | WO 2010/056337 | 5/2010 |
| WO | WO 01/82958 | 11/2011 |
| WO | WO 2013/016223 | 1/2013 |
| WO | WO 2014/028763 | 2/2014 |

OTHER PUBLICATIONS

Ahlskog, et al., *May Clin Proc*. 86:876-884, 2011.
Alvarez-Erviti: L et al. Delivery Of siRNA To The Mouse Brain By Systemic Injection Of Targeted Exosomes. *Nature Biotechnology*. 2011, vol. 29, pp. 341:345; abstract.
Bakhti et al., "Inhibition of Myelin Membrane Sheath Formation by Oligodendrocyte-derived Exosome-like Vesicles", *Journal of Biological Chemistry* 286(1):787-796, 2011.
Barca-Mayo et al., "Fine-Tuning Oligodendrocyte Development by microRNAs", *Frontiers in Neuroscience* 6(13):1-7; 2012.
Bernecker C, Ragginer C, Fauler G, Horejsi R, Moller R, Zelzer S, Lechner A, Wallner-Blazek M, Weiss S, Fazekas F, Bahadori B, Truschnig-Wilders M, Gruber HJ (2011) Oxidative stress is associated with migraine and migraine-related metabolic risk in females. *Eur J Neurol* 18:1233-1239.
Bobrie, et al., *Traffic* 12:1665-1668, 2011.
Caggiano AO, Kraig RP (1996) Eicosanoids & nitric oxide influence induction of reactive gliosis from spreading depression in microglia but not astrocytes. *J Comp Neurol* 369:93-108 (journal cover picture). PMCID: PMC2807127.
Christie-Pope BC, Mitchell HM, Kraig RP (2009) Deprenyl (selegiline) neuroprotection against excitotoxic injury in hippocampal slice cultures follows a hormetic dose-response pattern and depends on tumor necrosis factor-alpha. *Soc Neurosci* 35: Prog #744.14.
Cipolla MJ, Pusic AD, Grinberg YY, Chapman AC, Poynter ME, Kraig RP (2012) Pregnant serum induces neuroinflammation and seizure activity via TNFα. *Exp Neurol* 234:398-404. PMCID: PMC3304003.

(Continued)

*Primary Examiner* — J. E. Angell
(74) *Attorney, Agent, or Firm* — Norton Rose Fulbright US LLP

(57) ABSTRACT

Methods and compositions involving exosomes or lipid nanovesicles are provided. For example, certain aspects relate to compositions comprising exosomes obtained from cells that have been induced to undergo oxidative stress or stimulated. Furthermore, some aspects of the invention provide methods of treating a subject at risk or having a demyelinating disorder using the compositions.

20 Claims, 18 Drawing Sheets

(56) References Cited

OTHER PUBLICATIONS

Dugas JC, Cuellar TL, Scholze A, Ason B, Ibrahim A, Emery B, Zamanian JL, Foo LC, McManus MT, Barres BA (2010) Dicer1 and miR-219 Are required for normal oligodendrocyte differentiation and myelination. *Neuron* 65: 597-611.
Eijnden, SV et al. Preferential Production Of The IL-12(p40)/IL-23(p19) Heterodimer By Dendritic Cells From Human Newborns. *Cellular Immune Response*. 2006, vol. 36, pp. 21-26; abstract.
Eldh M, Ekstrom K, Valadi H, Sjostrand M, Olsson B, Jemas M, Lotvall J (2010) Exosomes communicate protective messages during oxidative stress; possible role of exosomal shuttle RNA. *PLoS'One* 5: e15353.
Extended European Search Report for EP 13829748.6, dated Dec. 9, 2015.
Fan Y, Pusic AD, Grinberg YY, Kraig RP (2012) Spreading depression is preceded by a rise in neuronal intracellular chloride. *Soc Neurosci* 38: Prog:#247.20.
Fitzner et al., "Selective transfer of exosomes from oligodendrocytes to microglia by macropinocytosis", *Journal of Cell Science* 124(3):447-458, 2011.
Flygt, et al., *Eur J Neurosci*, 2013.
Fruhbeis, C et al. Emerging Roles Of Exosomes In Neuron-GLia Communication. *Frontiers in Physiology*. 2012, vol. 3, pp. 1-5; abstract.
Grinberg et al., Insulin-like growth factor-1 lowers spreading depression susceptibility and reduces oxidative stress. *J Neurochem* 122:221-229, 2012.
Grinberg YY, Dibbern ME, Kraig RP (2012) Oxidative stress from spreading depression preferentially rises in astrocytes and microglia, with the latter effect mitigated by IGF-1. *Soc Neurosci* 38:#62.11.
Grinberg YY, Dibbern ME, Levasseur VA, Kraig RP (2013) Insulin-like growth factor-1 abrogates microglial oxidative stress and TNF-α responses to spreading depression *J Neurochem* 126:662-672. PMCID: PMC3752330.
Grinberg YY, Kraig RP (2011) Insulin-like growth factor-1 (and insulin) mitigates spreading depression susceptibility: implications for migraine therapy. *Soc Neurosci* 37: Prog #875.07.
Grinberg YY, Kraig RP (2013) Intranasal delivery of IGF-1 decreases spreading depression susceptibility in rat. Soc. Neurosci 39: Prog: #822.06.
Grinberg YY, Milton JG, Kraig RP (2010) Microglial cells search via Levy flights, with increased run lengths after TNF-α or reduced neuronal activity. Soc Neurosci 36: Prog #346.1.
Grinberg YY, Milton JG, Kraig RP (2011) Spreading depression sends microglia on Lévy flights. *PLoS ONE* 6:e19294. PMCID: PMC3082564.
Heh-In et al., "MicroRNAs in neuronal function and dysfunction", *Trends in Neuroscience* 35(5):325-334, 2012.
Howng SYB, Avila RL, Emery B, Traka M, Lin W, Watkins T, Cook S, Bronson R, Davisson M, Barres BA, Popko B. ZFP191 is required by oligodendrocytes for CNS myelination. *Genes and Development*, 24(3):301-11, 2010. PMC2811831.
Hulse RE, Swenson WG, Kunkier PE, White DM, Kraig RP (2008) Monomeric IgG is neuroprotective via enhancing microglial recycling endocytosis and TNF-α. *J Neurosci* 28:12199-12211. PMCID: PMC2699401.
International Search Report and Written Opinion for PCT/US13/55187, dated Dec. 16, 2013.
Kauer & Ling, *Prog Neurobiol*, 2009.
Kraig RP (2008) Migraine: Mechanisms and Management. *World Press*.
Kraig RP, Mitchell HM, Christie-Pope B, Kunkler PE, White DM, Tang YP, Langan G (2010) TNF-α and microglial hormetic involvement in neurological health & migraine. *Dose-Response* 8:389-413. PMCID: PMC2990060.
Kraig RP, Pusic AD, Pusic KM (2014) Exosomes from IFNγ-stimulated dendritic cells mitigate hypomyelination from hypoxic/ischemic injury modeled in brain slice culture. *Soc. Neurosci* 40: (in press).

Kunkier PE, Briant J, Hulse RE, Kraig RP (2006) Neural activity-dependent modulation of myelination, Soc Neurosci 32: #87.5.
Kunkier PE, Hulse RE, Schmitt MW, Nicholson C, Kraig RP (2005) Optical current source density analysis in hippocampal organotypic culture shows spreading depression occurs with uniquely reversing currents. *J Neurosci* 25:3952-3961. PMCID: PMC2712306.
Lauritzen et al., "Spreading Depression", *The Headaches*, Third Edition, pp. 269-274, 2006.
Lee, et al., *Semin Immunopathol* 33:455-467, 2011.
Li J-S & Yoa Z-X (2012) Mol Neurobiol.
Lin W and Popko B, Endoplasmic reticulum stress in disorders of myelinating cells. *Nature Neuroscience* 12(14): 379-85, 2009. PMC2697061.
Lin W, Bailey SL, Ho H, Harding HP, Ron D, Miller SD, Popko B: The integrated stress response prevents demyelination by protecting oligodendrocytes against immune-mediated damage, *Journal of Clinical Investigation* 117(2):448-456, 2007. PMC1783809.
Lin W, Kunkier PE, Harding HP, Ron D, Kraig RP, Popko B (2007) Enhanced integrated stress response promotes myelinating oligodendrocyte survival in response to interferon-γ. Soc Neurosci 33: Prog #117.7. (Abstract).
Lin, W. et al. Enhanced Integrated Stress Response Promotes Myelinating Oligodendrocyte Survival In Response To Interferon-gamma. *The American Journal of Pathology*. 2008, vol. 173, pp. 1508-1517; abstract; pa~e 1509; col. 1; paragraph 2.
Liu et al., *J Biol Chem* 273:11313-20, 1998.
Merkler et al., *Ann Neurol* 66:355-365, 2009.
Mitchell HM, Levasseur V, Kraig RP (2010) TNF-α increases spreading depression susceptibility via reduced GABAergic inhibition—implications for the transformation of episodic to chronic migraine. *Soc Neurosci* 36: Prog #346.3.
Mitchell HM, Pusic AD, Kraig RP (2011) Interleukin-11 mitigates spreading depression susceptibility: implications for migraine therapy. *Soc Neurosci* 37: Prog #875.22.
Mitchell HM, White DM, Domowicz MS, Kraig RP (2011) Cold pre-conditioning neuroprotection depends on TNF-α and is enhanced by blockade of interleukin-11. *J Neurochem* 117:187-196. PMCID: PMC3635118.
Mitchell HM, White DM, Kraig RP (2009) Cold-preconditioning neuroprotection of hippocampus follows a hormetic dose-response pattern initiated by tumor necrosis factoralpha from microglia and potentially evoked by adaptive interleukin-11 signaling from neurons. *Soc Neurosci* 35: Prog #744.4.
Mitchell HM, White DM, Kraig RP (2010) Strategies for study of neuroprotection from cold-preconditioning, *J Vis Exp* 43: doi: 10.3791/2192, PMCID: PMC3227089.
Montecalvo, A et al. Mechamsm Of Transfer Of Functional microRNAs Between Mouse Dendritic Cells Via Exosomes. *Blood*. 2012, vol. 119, pp. 756-766; abstract; p. 756, col. 1, paragraph 1; p. 764, col. 1, paragraph 2.
Moskowitz MA, Nozaki K, Kraig RP (1993) Neocortical spreading depression provokes the expression of cfos protein-like immunoreactivity within trigeminal nucleus caudalis via trigeminovascular mechanisms. *J Neurosci* 13:1167-1177, PMCID: PMC2737353.
Papadia et al., *Nat Neurosc* 11:476-487, 2008.
Podratz et al., *Glia*. 45:54-58, 2004.
Popko B. Myelin maintenance: axonal support required. *Nature Neuroscience* 13(3):275-7, 2010. PMID 20177417.
Popko B: Epigenetic Control of Myelin Repair. *Nature Neuroscience*. 2008 11(9):987-8, PMID: 18725899.
Powers, et al., *PNAS*, 110(11):4075-80, 2013.
Pusic AD Kraig RP (2010) Inflammatory gene micro array profiling demonstrates "T-cell-like" activation after recurrent spreading depression—implications for migraine pathogenesis. *Soc Neurosci* 36: Prog #346.2.
Pusic AD Pusic KM, Kraig RP (2013) IFNγ Stimulated dendritic cell exosomes as a therapeutic for remyelination. *Soc. Neurosci* 39: Prog: #812.02.
Pusic AD, Grinberg YY, Mitchell HM, Kraig RP (2011) Modeling neural immune signaling of episodic and chronic migraine using spreading depression in vitro. *J Vis Exp* 52: doi: 10.3791/2910.44.
Pusic AD, Kraig RP (2012) Exosome-mediated mitigation of oxidative stress and demyelination, *Soc Neurosci* 38:#157.01.

(56) References Cited

OTHER PUBLICATIONS

Pusic AD, Kraig RP (2014) Youth and environmental enrichment generate serum exosomes containing miR-219 that promote CNS myelination. *Glia* 62:284-299. PMID: 24339157. PMCID: pending.
Pusic AD, Kraig RP (2015) Phasic Treatment with Interferon Gamma Stimulates Release of Exosomes that Protect Against Spreading Depression. *J Interferon Cytokine Res* [epub ahead of print].
Pusic AD, Mitchell HM, Kraig RP (2011) IFN-γ from T-cells modulates susceptibility to- and transient demyelination from—spreading depression: implications for migraine therapy. *Soc Neurosci* 37: Prog #875.16.
Pusic AD, Mitchell HM, Kunkler PE, Klauer N, Kraig RP (2015) Spreading depression transiently disrupts myelin via interferon-gamma signaling, Exp Neurol 264:43-54.
Pusic AD, Pusic KM, Clayton, BL, Kraig RP (2014) IFNγ Stimulated dendritic cell exosomes as a potential therapeutic for remyelination. *J Neuroimmunol* 266:12-23. PMCID: PMC3920591.
Pusic AD, Pusic KM, Kraig RP (2014) Pro-myelinating serum-derived exosomes from environmentally enriched rats are secreted by peripheral blood mononuclear Cells. *Soc. Neurosci* 40: #22407.
Pusic AD, Pusic KM, Kraig RP (2014) What are exosomes and how can they be used in multiple sclerosis therapy? *Expert Rev Neurotherapeutics* 14:353-355.
Pusic et al., "IFNγ-stimulated dendritic cell exosomes as a potential therapeutic for remyelination", *Journal of Neuroimmunology* 266:12-23; 2014.
Pusic KM, Pusic AD, Kraig RP (2013) Microglia are essential for synaptically induced spreading depression, *Soc. Neurosci* 39: Prog: #133.07.
Pusic KM, Pusic AD, Kraig RP (2014) Nasal administration of IFNγ-stimulated dendritic cell Exosomes inhibits spreading depression, *Soc. Neurosci* 40: #22408.
Pusic KM, Pusic, AD, Kemme J, Kraig RP (2014) Spreading depression requires microglia and is decreased by their M2a polarization from environmental enrichment. *Glia* 62:1176-1194. PMID: 24723305. PMCID.
Pusic, et al., GLIA, 62(2): 284-299, 2014.
Radak et al., *Free Radic Biol Med*. 44:153-159, 2008.
Ruckh, et al., *Cell Stem Cell*, 10(1):96-103, 2012.
Skog, et al., *Nat Cell Biol*. 10:1470-1476, 2008.
Sohal & Weindruch, *Science*. 5:59-63, 1996.
Somjen GG (2001) Mechanisms of spreading depression and hypoxic spreading depression-like depolarization. *Physiol Rev* 81: 1065-1096.
Traka M, Arasi K, Avila RL, Podojil JR, Miller SD, Soliven B and Popko B. A genetic mouse model of adultonset, pervasive CNS demyelination with robust remyelination. Brain, 133(10):3017-29, 2010. PMID 20851998.
Tuncel D, Tolun FI, Gokee M, Imrek S, Ekerbicer H (2008) Oxidative stress in migraine with and without aura. *Biol Trace Elem Res* 126: 92-97.
Valadi, et al., *Nat Cell Biol*. 9:654-659, 2007.
Viaud, et al., J. Immunother, 34(1), Jan. 2011.
Viggiano A, Viggiano E, Valentino I, Monda M, Viggiano A, De Luca B (2011) Cortical spreading depression affects reactive oxygen species production. *Brain Res* 1368: 11-18.
Wheeler et al., 2001.
Zhao, et al., *Anat Rec*, 6:999-1005, 2012.
Zhuang X, Xiang X, Grizzle W, Sun D, Zhang S, Axtell RC, Ju S, Mu J, Zhang L, Steinman L, Miller D, Zhang HG (2011) Treatment of brain inflammatory diseases by delivering exosome encapsulated anti-inflammatory drugs from the nasal region to the brain. *Mol Ther* 19: 1769-1779.
Ziv, et al., *Nat Neurosci* 9:268-275, 2006.

\* cited by examiner

EXOSOME-BASED THERAPEUTICS AGAINST NEURODEGENERATIVE DISORDERS

CROSS-REFERENCE TO RELATED APPLICATIONS

This application is a continuation of U.S. patent application Ser. No. 14/420,680 filed Feb. 10, 2015, which is a national phase application under 35 U.S.C. § 371 of International Application No. PCT/US2013/055187, filed Aug. 15, 2013, which claims the benefit of priority to U.S. Provisional Patent Application Serial No. 61/683,596, filed Aug. 15, 2012. The entire contents of each of the above-referenced disclosures are specifically incorporated herein by reference without disclaimer.

This invention was made with government support under grants NS019108, HD009402, and TR000918 awarded by the National Institutes of Health. The government has certain rights in the invention.

BACKGROUND

1. Field of the Invention

The present invention relates generally to the field of medicine and neurology. In particular, embodiments are directed to treatment of demyelinating disorders such as multiple sclerosis (MS) and other neurological disorders associated with demyelination.

2. Description of Related Art

MS is a common neurological disease affecting more than 1 million people worldwide. Its prevalence rate varies between races and geographical latitude, ranging from more than 100 per 100,000 in Northern and Central Europe to 50 per 100,000 in Southern Europe. MS is the most common cause of neurological disability in young and middle-aged adults. Disease onset is before the age of 30 in about 50% of patients, between the ages of 30 to 40 in 25% of the patients, and between the ages of 40 to 50 in the remaining 25% of patients. The female to male ratio is 2:1.

Neurological damage caused by MS can have a major physical, psychological, social and financial impact on the patients and on their families. The most common clinical symptoms of MS are paresis, paraesthesia, visual impairment, sexual, bowel, and urinary dysfunction, spasticity, and incoordination. Cognitive dysfunction occurs in 40 to 50% of patients. The extent of neurological deficit, rate of progression, and frequency of relapses are highly variable among affected individuals.

Existing therapies for MS are designed to reduce inflammation and thus reduce the degree of demyelination, and in some cases promoting remyelination. However, there remains a need for a therapy that not only curtails demyelination, but also significantly promotes myelination and reduces oxidative stress (OS). Such a therapy would be instrumental in treating neurodegenerative disorders such as MS, as well as cognitive decline from normative aging.

SUMMARY OF THE INVENTION

Aspects of the present invention overcome a major deficiency in the art by providing novel methods involving exosomes (which are referred to here as exosomes, lipid nanovesicles, or nanovesicles) that may promote myelination or repair demyelination, and can be modified or loaded to contain particular nucleic acid molecules (such as mRNAs and/or miRNAs) and/or proteins identified in these exosomes.

Accordingly, in a first embodiment there is provided a method for treating a patient at risk for or having a demyelinating disorder. The method may comprise administering to the patient an effective amount of a pharmaceutical composition comprising isolated exosomes obtained from cells that have been induced to undergo or stimulated via oxidative stress or lipid nanovesicles (e.g., exosomes) that have the same or substantially similar composition as such exosomes. The composition may further comprise a pharmaceutically acceptable carrier.

Non-limiting examples of the demyelinating disorder include cognitive decline from aging, Alzheimer's disease, Parkinson's disease, stroke, epilepsy, migraine, multiple sclerosis, and neuropathy. Also specifically contemplated are traumatic and ischemic brain injury, which can result in a significant loss of myelin. In particular examples, the demyelinating disorder is multiple sclerosis, neuropathy, traumatic brain injury, or neonatal brain injury.

In some embodiments, the compositions can be administered to a subject by any method known to those of ordinary skill in the art. Examples include intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, directly into a heart chamber, directly injected into the organ or portion of organ or diseased site of interest, or by other method or any combination of the forgoing as would be known to one of ordinary skill in the art. In a particular aspect, the composition can be administered nasally or intravenously. In some embodiments, the composition is a liquid. In other embodiments, the composition is a gel or a powder. It is specifically contemplated that the composition may be a liquid that is provided to the patient as a mist.

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 445, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of exosomes, or any range derivable therein. The above numerical values may also be the dosage that is administered to the patient based on the patient's weight, expressed as ng/kg, mg/kg, or g/kg, and any range derivable from those values.

Alternatively, the composition may have a concentration of exosomes that are 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 ng/ml, µg/ml, mg/ml, or g/ml, or any range derivable therein.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a demyelinating disorder.

In certain embodiments, the isolated exosomes may include one type or at least two, three, four, five, six, seven, eight, nine, ten or more different types of exosomes. The type of exosomes may be characterized by their compositions, for example, the types of nucleic acids and/or proteins of interest or effects.

The cells for producing exosomes can be any cells of one or more subjects. For example, the cells may be immune cells, neural cells, or adipose cells. In particular aspects, the cells may be immune cells, such as dendritic cells, lymphocytes (T cells or B cells), macrophages, or any cells of the immune system.

In a particular aspect, the cells for producing exosomes can be neural cells, such as microglia, astrocytes, neurons, oligodendrocytes, spindle neurons or any cells of the nervous systems. The cells can be in the form of a cell culture, a dissected tissue, or parts thereof. For example, the cells can be in the form of hippocampal slice cultures.

In certain aspects, the cells have been induced to undergo or stimulated by oxidative stress before the collection of exosomes. The oxidative stress can be induced by an exogenous cytokine, such as IFN-γ or TNF-α, or other cytokines from T-cells, or an oxidant such as hydrogen peroxide. In some embodiments, the cells have been induced by a cytokine or an oxidant. In some embodiments, the cells have been stimulated by a cytokine or an oxidant.

In a certain embodiment, the composition may be an autologous composition or the cells may be obtained from the same patient to be treated. Particularly, cells from a human subject may be harvested and cultured, and induced, stimulated or engineered to secrete an effective exosome-containing composition according to certain aspects of the invention. The exosome-containing composition may be then administered in a pharmaceutical composition to the same human donor.

In this particular embodiment, all the advantages of the autologous donation can apply. The skilled person will choose the nature and identity of the donor tissue or cells for exosome production depending on the use and as is expedient. Here, it may be necessary to consider the criteria and the advantages relevant for the decision to use autologous donation, and/or the choice of donor tissue/cells.

In another embodiment, the composition may be allogenic, that is to that the say donor organism that provides exosome-producing cells and recipient organism to be treated are the same species but different individuals.

In an alternative embodiment, the composition may be xenogenic. This means that it is taken from an organism of a different species. For this purpose, cells are taken from a donor organism, for example an animal such as a rat or yeast, and are induced, stimulated or engineered to produce an effective exosome-containing composition, which is administered in a pharmaceutical composition to the individual to be treated which belongs to a different species, for example a human.

The cells for producing exosomes may be obtained from a subject that is relatively young, for example, at an age that is at most one tenths, one fifths, one third, or half of the subject's expected life span. For example, the exosomes may be obtained from a human that is at most, less than or about one, two, three, four, five, six, seven, eight, nine, ten, 11, 12 months, or 1, 2, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 years old, or any age or range derivable therein. In a particular aspect, the exosomes may be obtained from a human that is less than one year old or less than 18 years old. In a particular aspect, the exosomes may be obtained from a human that is between 18 and 50 years old. The human may be the same patient that is to be treated.

Furthermore, in some aspects, the isolated exosomes or nanovesicles (e.g., the artificially engineered exosomes from in vitro reconstitution) may contain endogenous exosomes or may be loaded with externally added therapeutic agents, such as nucleic acids or protein molecules. The nucleic acids may be DNA or RNA, such as siRNA, miRNA, or mRNA. In certain aspects, the isolated exosomes may comprise miRNAs such as one or more of miR-7a, miR-9, miR-9*, miR-17, miR-18a, miR-19a, miR-19b, miR-20a, miR-92a-1, miR-23a, miR-23a*, miR-23b, miR-32, miR-128, miR-138, miR-138*, miR-184, miR-199a-5p, miR-214, miR-219, miR-338, miR-338*, miR-27a, miR-27b, miR-106a, miR-124, miR-141, miR-144, miR-145, miR-146a, miR-181a, miR-200a, miR-451, miR-532-5p, and miR-665. In certain aspects, the isolated exosomes may comprise proteins or mRNAs that encode antioxidant system proteins or miRNAs involved in oxidant/antioxidant homeostasis. In some embodiments, the externally added therapeutic agent is an engineered siRNA, mRNA, or miRNA (or combination of these agents) involved in oligodendrocyte differentiation and/or oxidant/antioxidant homeostasis that is added to naïve exosomes.

In certain aspects, the nanovesicles or loaded exosomes may comprise miRNAs such as one or more of miR-219, miR-138, miR-199a-5p, and/or miR-338. In certain aspects, the nanovesicles may comprise proteins or mRNAs that encode antioxidant system proteins.

The mRNA may encode antioxidant system proteins, such as enzymatic antioxidants (e.g., superoxide dismutase (SOD) or secreted antioxidants (e.g., glutathione). The skilled artisan will understand that methods for direct loading of agents, chimeric loading of agents, or indirect loading (through modification of the producing cells) may be used. A particular example of direct loading may be via electroporation.

There may also be provided methods for obtaining isolated exosomes of cells. For example, the cells may be neural cells. In other aspects, the cells may be immune cells. The methods may involve obtaining the cells that have been induced to undergo or stimulated via oxidative stress, where the cells produce exosomes. The methods may further involve isolating the produced exosomes.

As described above, the isolated exosomes may be comprised in pharmaceutical compositions for the treating of a patent at risk for or having a demyelinating disorder, such as cognitive decline (e.g, from aging), Alzheimer's disease, Parkinson's disease, stroke, epilepsy, migraine, multiple sclerosis, neuropathy, traumatic brain injury, and neonatal brain injury. In particular examples, the demyelinating disorder is multiple sclerosis, neuropathy, migraine, traumatic brain injury, or neonatal brain injury.

In certain aspects, the method may further comprise culturing the cells under conditions to induce oxidative stress before the isolation of exosomes. The oxidative stress can be induced by an externally added cytokine, such as IFN-γ, by any other activating cytokines such as tumor necrosis factor alpha, or by an oxidant such as hydrogen peroxide.

In other aspects, the compositions may comprise lipid nanovesicles that contain the same types or substantially similar types of nucleic acids such as mRNA, miRNAs, or proteins as those found in the isolated exosomes. The miRNAs may be one or more of miR-7a, miR-9, miR-9*, miR-17, miR-18a, miR-19a, miR-19b, miR-20a, miR-92a-1, miR-23a, miR-23a*, miR-23b, miR-32, miR-128, miR-138, miR-138*, miR-184, miR-199a-5p, miR-214, miR-219, miR-338, miR-338*, miR-27a, miR-27b, miR-106a, miR-124, miR-141, miR-144, miR-145, miR-146a, miR-181a, miR-200a, miR-451, miR-532-5p, and miR-665. In some embodiments, the miRNAs may be one or more of miR-219, miR-138, miR-199a-5p, miR-338, miR-181a, miR-451, miR-532-5p, and miR-665. In certain aspects, the nanovesicles may be exosomes isolated from cells, like human cells, more particularly, a human that is at risk for or has a demyelinating disorder. In other aspects, the nanovesicles may be prepared from in vitro reconstitution of lipids. In other aspects, the nanovesicles may be loaded with one or more of the miRNAs listed above. The compositions may be comprised in pharmaceutical compositions and used for treating of subjects at risk for or having a demyelinating disorder. The nanovesicles may have a diameter of at least, about, or at most, 1, 2, 3, 4, 5, 10, 15, 20, 30, 40, 50, 60, 70, 80, 90, 100, 150, 200, 250, 300, 350, 400, 450, 500, 550, 600, 650, 700, 750, 800, 850, 900, 950, 1000 nm or any range derivable therein. In a particular aspect, the exosome or vesicles may have a diameter of about 40 to about 100 nm. As used herein, "substantially similar" refers to at least 50, 55, 60, 65, 70, 75, 80, 90, 95, 99 or 100% identical or any range derivable therein.

Embodiments discussed in the context of methods and/or compositions of the invention may be employed with respect to any other method or composition described herein. Thus, an embodiment pertaining to one method or composition may be applied to other methods and compositions of the invention as well. For example, any of the disclosed methods of administration may be used to treat any of the disclosed demyelinating disorders. Thus, embodiments of the invention include methods of treating patients having multiple sclerosis using a nasal administration route, an intravenous administration route, an inhalation administration route, or any other administration route. In other embodiments, the same routes of administration are used to treat patients with Alzheimer's disease, Parkinson's disease, stroke, or any other demyelinating disorder. As a further example, embodiments of the invention include treating multiple sclerosis with exosomes comprising miRNAs. Further embodiments of the invention include treating Alzheimer's disease, Parkinson's disease, stroke, or any other demyelinating disorder with exosomes comprising miRNAs. Further embodiments of the invention include treating multiple sclerosis with exosomes comprising mRNAs encoding antioxidant system proteins. Still further embodiments of the invention include treating Alzheimer's disease, Parkinson's disease, stroke, or any other demyelinating disorder with exosomes comprising mRNAs encoding antioxidant system proteins.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Throughout this application, the term "effective" or "effective amount" is used to indicate that the compounds are administered at an amount sufficient to treat a condition in a subject in need thereof.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein the terms "encode" or "encoding" with reference to a nucleic acid are used to make the invention readily understandable by the skilled artisan; however, these terms may be used interchangeably with "comprise" or "comprising" respectively.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 11A-11D. Representative images show that glutathione-related fluorescence was assessed via ThiolTracker™ under (A) control conditions and (B) the drop in glutathione evident 30 minutes after incubation with IFN-γ (500 U/mL). (C) Seven days after exposure to a 12-hour pulse of IFN-γ, glutathione content had recovered from the initial drop, and increased above baseline. (D) Treatment with exosomes from IFN-γ-stimulated slice cultures produced an even more robust increase. (E) In each case, these exposures were significantly (p<0.01, 0.001, and 0.001, respectively) different from control. (F) High power microscopy showed that glutathione-positive cells were about 10 µm in diameter, suggesting they were microglia. Confocal imaging and labeling of microglia with isolectin-GS-IB4 confirmed this suggestion. An exemplary image is shown. Arrowheads point to microglial surfaces and arrows to glutathione containing cell bodies. Numerical data are mean±SEM and significance (*p<0.05). Scale bar=10 µm. Comparisons between groups made via ANOVA plus Holm-Sidak post hoc testing.

DESCRIPTION OF ILLUSTRATIVE EMBODIMENTS

I. Introduction

Figure 1:
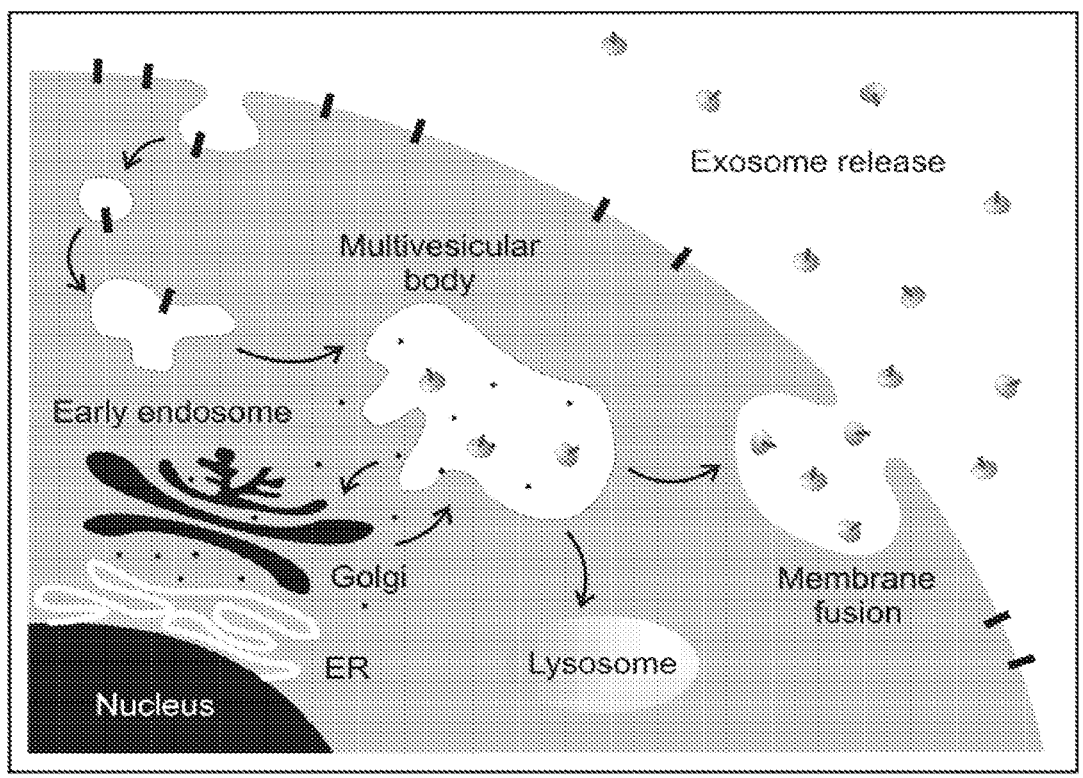
FIG. 1: Schematic of exosome formation. Exosomes form by invagination of the membrane of endocytic compartments, leading to formation of small interluminal vesicles that form as the endosome matures to become the multivesicular body (MVB). Molecular aggregation of surface receptors reroutes them to the MVB instead of the recycling compartment. Proteins and nucleic acids are specifically sorted to the MVB during biogenesis. The MVB can fuse with a lysosome, which leads to degradation of its contents, or with the plasma membrane to release them. When the MVB fuses with the cell's plasma membrane, interluminal vesicles are released as exosomes into the interstitial space.

In some aspects, the invention generally relates to methods and compositions involving lipid nanovesicles, such as vesicles reconstituted in vitro, or exosomes obtained from cells that have been induced to undergo or stimulated via oxidative stress. The methods and compositions are suitable for treating subjects at risk for or having a neurological disorder, particularly a demyelination disorder. The invention is partly based on the discovery that certain exosomes, such as exosomes from cells that have been induced under or stimulated via oxidative stress, can enhance myelination capacity.

These methods and compositions have important improvements over existing state-of-the-art. In certain embodiments, the inventors describe development of a naturally occurring process (i.e., youth and environmental enrichment, which can be mimicked via an oxidation signal such as cytokine exposure or oxidant exposure to stimulate blood-borne exosomes and related oxidative stress induction) as a novel treatment strategy for demyelinating disorders, including degenerative neurological disorders.

In certain embodiments of the invention, naturally occurring exosomes, small vesicles secreted by cells, can reduce oxidative stress (OS) and promote myelination by facilitating intercellular communication—even across the blood brain barrier. To the inventors' knowledge, no other treatments provide this combination. Exosomes can potentially enter all cell types and importantly, can cross the blood brain barrier when administered intravenously or nasally. Furthermore, they may be targeted to specific cell types.

Existing therapies for MS are designed to reduce inflammation, thus reducing the degree of demyelination, and in some cases promoting remyelination. Advantages of certain embodiment of the invention include improving recovery from demyelination (e.g., by >44%), promoting myelination above control levels, and reducing OS—an underlying factor in the pathogenesis of MS and cognitive decline from aging.

For example, the methods and compositions in certain embodiments show a 40-45% reduction in OS, a 300-800% increase in O4 positive oligodendrocyte precursor cells, a 25-600% increase in O1 positive oligodendrocyte precursor cells, and a 50% increase in myelin basic protein (MBP) when compared to controls. Additionally, the threshold of spreading depression, a likely cause of migraine that was recently shown to trigger demyelination, is elevated by more than 200-fold upon stimulation by the methods and compositions. Collectively, these nutritive changes illustrate the robust effect of the methods and compositions in some embodiments.

In certain embodiments, the methods and compositions enhance naturally occurring signaling pathways, and thus are likely to have a considerably better benefit/risk profile. This is especially important considering the elevated risk of infection posed by use of existing immunomodulating therapies for MS. Finally, the methods and compositions in certain embodiments may be a novel therapy for MS, as well as for treatment of other CNS degenerative disorders whose pathogenesis involves OS and oligodendrocyte injury/dysmyelination.

II. Definitions

"Exosomes" are nanovesicles released from a variety of different cells. These small vesicles may be derived from large multivesicular endosomes and secreted into the extracellular milieu. The precise mechanisms of exosome release/shedding remain unclear. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions in some aspects may be administered in a sufficient amount to produce a at a reasonable benefit/risk ratio applicable to such treatment.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

III. Exosomes

In certain aspects of the invention, exosomes may be prepared and used as a novel therapeutic modality for improvement of brain health or other related diseases.

Exosomes were first described as a means for reticulocytes to selectively discard transferrin receptors as they matured into erythrocytes (Johnstone, et al., 1987). For a long time thereafter, they were seen as mere 'garbage cans' for the removal of unwanted cellular components. However, since the discovery that B cells shed exosomes containing antigen-specific MHC II capable of inducing T cell responses (Raposo, et al., 1996), an abundance of exosome research has revealed that these small vesicles are involved in a multitude of functions, both physiological and pathological.

Exosomes are small membrane vesicles of endocytic origin that are secreted by many cell types. For example, exosomes may have a diameter of about 40 to about 100 nm. They may be formed by inward budding of the late endosome leading to the formation of vesicle-containing multivesicular bodies (MVB) which then fuse with the plasma membrane to release exosomes into the extracellular environment. Though their exact composition and content depends on cell type and disease state, exosomes all share certain characteristics.

In certain aspects, the exosomes may be purified by ultracentrifugation in a sucrose gradient, then identified by the presence of marker proteins such as Alix and CD63 (Schorey & Bhatnagar, 2008) or enrichment of tetraspanins and heat shock protein 70 (Lee, et al., 2011), all of which are specifically expressed on exosomes. Furthermore, exosomes can be isolated in vivo from malignant effusions and normal body fluids such as urine, blood, and cerebrospinal fluid, making them a promising source of diagnostic biomarkers. In some other aspects, exosomes can be isolated using ExoQuick-TC™ isolation kits.

Exosomes also have the potential for directional homing to specific target cells, dependent on the physical properties of their membranes. Their effect can be local, regional or systemic. Exosomes do not contain a random sampling of their parent cell's cytoplasm, but are enriched in specific mRNA, miRNA and proteins (Bobrie, et al., 2011). This cargo is protected from degradation by proteases and RNases while the vesicle is in the interstitial space, and retains bioactivity once taken up by a recipient cell. In this way, they facilitate the transfer of interactive signaling and enzymatic activities that would otherwise be restricted to individual cells based on gene expression (Lee, et al., 2011). For example, Skog and coworkers show that mRNA for a reporter protein can be incorporated into exosomes, transferred to a recipient cell, and translated (Skog, et al., 2008).

According to certain aspects, the exosomes and compositions can be produced using various preparations of cells. For example, the exosome-producing cells may be cultured with cytokines or other reagents to induce oxidative stress, for example, cultured in the presence of interferon gamma (IFNγ), IL1-α, β, IL-2, IL-7, IL-12, IL-15, IL-18, IL-4 and/or IL-13; and/or antibodies against T cells surface markers, such as CD2, CD3, CD28, TCR, and/or soluble MHC class I or II tetramers and/or soluble CD1 tetramers. In a particular aspect, the exosome-producing cells may be cultured in the presence of IFNγ. The culturing may comprise acute treatment or phasic treatment of cells with reagents.

In another particular embodiment, the cells may be immune cells such as T cells. The T cells may have been cultured in the presence of a TCR-activating agent, or any one or more T cell subsets, such as $CD4^+$ T cells, $CD8^+$ T cells, γδT cells, NKT cells, or for NK cells. Particularly preferred T cell subsets for delivering MHC Class I/II peptides are $CD4^+$ T cells and $CD8^+$ T cells. NK cells may also produce exosomes in certain aspects. In additional aspects, the cell may be cultured with pharmaceutical reagents or particular treatments to induce maturation and/or activation of the cells, for example, in the presence of antigens, autologous or allogeneic APCs loaded with specific antigens or superantigens, mitogens (i.e., PHA), agrin, antibodies (such as anti-CD3 and anti-CD28 antibodies) or fragments thereof, reagents that trigger the activation of PKC (i.e., phorbol esters), cytoplasmic $Ca^{2+}$ release (i.e., calcium ionophores), inhibition of phosphatases (i.e., okadaic acid) etc. In a particular embodiment, the cells may have been expanded and/or activated in culture.

In a further embodiment, the cells may be neural cells, such as glial cells, astrocytes, neurons, oligodendrocytes, spindle neurons, microglia, or any cells of the nervous systems. The cells can be in the form of a cell culture, a dissected tissue, or parts thereof. For example, the cells can be in the form of hippocampal slice cultures.

Furthermore, in a particular embodiment, the cells are autologous with respect to the patient to be treated, although allogeneic or even xenogeneic cells may be used. In a further particular embodiment, the cells may produce a recombinant polynucleotide encoding a biologically active molecule. This embodiment will be disclosed in more details below.

The exosomes produced or released by cells may be isolated and/or purified using several techniques. These include filtration, centrifugation, ion-chromatography, or concentration, either alone or in combinations. An exemplary purification method comprises a step of density gradient centrifugation. Another exemplary method comprises a step of ultrafiltration, either alone or coupled to a centrifugation step. Suitable purification methods have been described in WO99/03499, WO00/44389 and WO01/82958, which are incorporated therein by reference.

Selective purification or enrichment of physiologically active subpopulations of exosomes may be achieved via several procedures. In certain embodiments, effective exosomes may be concentrated to an enriched sample via use of specific surface protein markers and related separation techniques. In other embodiments, effective exosomes may be harvested from enriched primary cells cultures identified as capable of producing the effective exosomes. In further embodiments, based on screening procedures used to identify candidate effective exosome species, other exosomes may be fabricated using molecular engineering strategies designed to selectively produce exosomes containing the target (i.e., postulated) therapeutic molecular species. The latter may be confirmed by application of exosomes containing fabricated species to naïve cultures, where the desired effect (e.g., increased myelination) may be verified.

In certain embodiments, the exosomes or vesicles may be loaded with therapeutic agents such as nucleic acid molecules. The methods may include, but are not limited to:

(a) Electroporation. By this method, a number of holes are made in cells/exosomes by briefly shocking them with an electric field of 100-200 V/cm. The DNA/RNA can enter the cells/exosomes through the holes made by the electric field.

(b) Lipofection. The method commonly called transfection and can be used to transform cells/exosomes with DNA/RNA via vesicles containing the desired genetic constructs. The vesicles fuse with the cell membrane (similar to how two oil spots at the top of a broth will fuse) and the contents of the vesicles and the cells are combined. There are a number of transfection kits in the market, ready for use, e.g. DeliverX siRNA Transfection Kit (cat. No. DX0002) from Panomics, FuGENE® HD Transfection Reagent (Cat. no. 04709691001) from Roche and LIPOFECTAMINE™ 2000 (Cat. No. 11668-027) from Invitrogen.

(c) Transformation using heat shock. Chilling cells/exosomes in the presence of divalent cations such as $Ca^{2+}$ (in $CaCl_2$) makes their membranes become permeable to RNA or DNA plasmids or fragments. Cells or exosomes are incubated with the DNA and then briefly heat shocked (42° C. for 30-120 seconds), which causes the DNA to enter the cell. This method may work well for condensed circular plasmid DNAs and may work for exosomal or lipid nanovesicle constituents.

The above methods describe briefly how production and delivery of modified exosomes can be achieved to transfer RNA and DNA to recipient cells. Exosomes can be engineered to contain RNA/DNA or modified to contain the gene of interest and may be isolated and shifted to the recipient cells, to affect their biological function or survival. Consequently, the exosomes may dispose their content into the cytoplasm of the target cells, which in turn leads to translation of mRNA to specific proteins in the target cell. Further, exosomes are capable of carrying and transferring small coding and non-coding RNA such as microRNA and siRNA that may regulate translation of a specific gene.

Modified or loaded exosomes being vesicles as carriers of DNA or RNA as described herein can be used to treat inherited diseases in hematopoietic, non-hematopoietic, stem cells, and organs. Modified or loaded exosome vesicles can also be used as carriers of DNA or RNA constructs for treatments of microbiological infections or diseases or dysfunctions in humans or animals, or for transfer through any biological membrane.

Changing or modifying the genetic material of exosomes by altering the conditions for the exosome-producing cells is achieved by changing pH, temperature, growing conditions, or using antibodies/chemicals toward exosome-producing cells. This results in alteration of the nucleic acid content. Also, over-expression or repression of cytokines, chemokines and other genes in the exosome-producing cells can be used to change or modify the content of exosomes.

Transferring sense or anti-sense RNA to specific cells using exosome vesicles to switch off genes instead of adding new ones results in down regulation (slow down) or prevention of translation of the particular gene. The method is called RNA interference (siRNA).

To administer nucleic acids to recipient cells or tissues, DNA or RNA-containing exosomes can be administered to cells by addition of the exosomes to cell cultures in vitro, or injection of these exosomes intravenously, or by any other route, in vivo as is known in the art, such as nasally or intravenously. Exosomes can be targeted to any cell in the body, including cells in the cardiovascular system, skeletal muscle cells, joint cells, neural cells, gut cells, lung cells, liver cells or kidney cells, or cells in the immune system, or to any type of cell with any function or dysfunction in the body of humans or animals, including malignant cells.

As disclosed in the invention herein, exosomes can be used to deliver genetic material to recipient cells to produce any drug or precursor of any drug, or to affect the function or metabolism of any drug, in any cell in humans or animals.

IV. miRNAs

In certain embodiments of the invention, isolated exosomes or lipid nanovesicles comprising microRNAs (abbreviated miRNAs) may be used in methods and compositions for treating patients at risk for or having demyelinating disorders. In particular embodiments, the miRNAs may include one, two, or all of miR-7a, miR-9, miR-9*, miR-17, miR-18a, miR-19a, miR-19b, miR-20a, miR-92a-1, miR-23a, miR-23a*, miR-23b, miR-32, miR-128, miR-138, miR-138*, miR-184, miR-199a-5p, miR-214, miR-219, miR-338, miR-338*, miR-27a, miR-27b, miR-106a, miR-124, miR-141, miR-144, miR-145, miR-146a, miR-181a, miR-200a, miR-451, miR-532-5p, and miR-665. In particular embodiments, the miRNAs may include one, two, or all of miR-219, miR-138, miR-338, and miR-199a-5p. For example, the miRNAs may be miR-219 and miR-138; the miRNAs may be miR-219 and miR-338; the miRNAs may be miR-219 and miR-199a-5p.

As disclosed herein, specific miRNAs (miR-219, miR-138, miR-338, and miR-199a-5p) were selectively enriched in young exosomes, particularly miR-219, which showed the most significant enrichment, and is known to affect multiple steps of OPC differentiation into mature, myelinating oligodendrocytes.

miRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression.

There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end.

The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance toward gaining apoptosis signaling.

V. Diseases

Diseases to be prevented, treated or diagnosed can be any disease that affects a subject that would be amenable to therapy or prevention through administration of a composition or a method as described herein. For example, the disease may be a disease amenable to the therapy for administering an exosome or lipid nanovesicle containing nucleic acids or other therapeutic agents that increase resistance to oxidative stress. In particular examples, there may be provided methods and compositions involving administering compositions involving isolated exosomes from cells that have been induced to undergo or stimulated via oxidative stress for treating demyelinating disorders.

A demyelinating disorder is any disorder or disease of the nervous system in which the myelin sheath of neurons is damaged. This impairs the conduction of signals in the affected nerves, causing impairment in sensation, movement, cognition, or other functions depending on which nerves are involved. The term describes the effect of the disease, rather than its cause; some demyelinating diseases are caused by genetics, some by infectious agents, some by autoimmune reactions, some by traumatic or ischemic injury, and some by unknown factors. Organophosphates, a class of chemicals which are the active ingredients in commercial insecticides such as sheep dip, weed-killers, and flea treatment preparations for pets, etc., will also demyelinate nerves. Neuroleptics can cause demyelination.

Non-limiting examples of demyelinating disorders of the central nervous system include: multiple sclerosis (together with the similar diseases called idiopathic inflammatory demyelinating diseases), cognitive decline from aging, migraine, Vitamin B12 deficiency, Central pontine myelinolysis, Tabes Dorsalis, transverse myelitis, Devic's disease, progressive multi focal leukoencephalopathy, Optic neuritis, Leukodystrophies, traumatic brain injury and neonatal brain injury. Non-limiting examples of demyelinating disorders of the peripheral nervous system include: Guillain-Barré syndrome and its chronic counterpart, chronic inflammatory demyelinating polyneuropathy, Anti-MAG peripheral neuropathy, Charcot-Marie-Tooth Disease, and Copper deficiency.

Demyelination is the act of demyelinating, or the loss of the myelin sheath insulating the nerves. When myelin degrades, conduction of signals along the nerve can be impaired or lost, and the nerve eventually withers. This leads to certain neurodegenerative disorders like multiple sclerosis and chronic inflammatory demyelinating polyneuropathy.

Central nervous system (CNS) demyelination is a cause and consequence of a variety of neurological diseases and especially exemplified by MS and cognitive decline from aging, which follow a relapsing-remitting but then progressive course and a more protracted but progressive course, respectively. In both instances, these maladies involve increased oxidative stress (OS), which damages brain cells of oligodendrocyte lineage that are responsible for brain myelination, and production of myelination inhibitory factors including specific miRNAs.

According to an embodiment of the invention, the methods described herein are useful in inhibiting the development of and/or treating multiple sclerosis. Multiple sclerosis (MS), also known as "disseminated sclerosis" or "encephalomyelitis disseminata", is an inflammatory disease in which the fatty myelin sheaths around the axons of the brain and spinal cord are damaged, leading to demyelination and scarring as well as a broad spectrum of signs and symptoms. Disease onset usually occurs in young adults, and it is more common in women. It has a prevalence that ranges between 2 and 150 per 100,000.

Demyelination may also play an important role in the pathophysiology of traumatic brain injury. In experimental studies, brain injuries have been shown to be accompanied by a loss of myelin (Johnson, et al., 2013).

Neonatal brain disorders are also associated with demyelination and failure of remyelination. White matter injuries in the newborn brain, such as hypoxic ischemic encephalopathy and periventricular leukomalacia can result in cerebral palsy and cognitive disability. Failure of remyelination in such conditions contributes to permanent demyelinated lesions. (Fancy, et al., 2011).

VI. Therapeutic Agents or Diagnostic Agents for Exosomes

In some embodiments, therapeutic agents or diagnostic agents may be loaded to the exosomes for delivery to a subject, such as by electroporation or other method known in the art. The therapeutic agents may be a therapeutic nucleic acid, a protein or antibody fragment, or a small molecule.

A "therapeutic nucleic acid" is defined herein to refer to a nucleic acid which can be administered to a subject for the purpose of treating or preventing a disease. The nucleic acid is one which is known or suspected to be of benefit in the treatment of a disease or health-related condition in a subject.

Therapeutic benefit may arise, for example, as a result of alteration of expression of a particular gene or genes by the nucleic acid. Alteration of expression of a particular gene or genes may be inhibition or augmentation of expression of a particular gene (e.g., via miRNA). In certain embodiments, the therapeutic nucleic acid encodes one or more proteins or polypeptides that can be applied in the treatment or prevention of a disease or health-related condition in a subject (i.e., via mRNA). The terms "protein" and "polypeptide" are used interchangeably herein. Both terms refer to an amino acid sequence comprising two or more amino acid residues.

Any nucleic acid known to those of ordinary skill in the art that is known or suspected to be of benefit in the treatment or prevention of a disease or health-related condition is contemplated in certain aspects as a therapeutic nucleic acid. The phrase "nucleic acid sequence encoding," as set forth throughout this application, refers to a nucleic acid which directs the expression of a specific protein or peptide. The nucleic acid sequences include both the DNA strand sequence that is transcribed into RNA and the RNA sequence that is translated into protein. In some embodiments, the nucleic acid includes a therapeutic gene. The term "gene" is used to refer to a nucleic acid sequence that encodes a functional protein, polypeptide, or peptide-encoding unit.

As will be understood by those in the art, the term "therapeutic nucleic acid" includes genomic sequences, cDNA sequences, and smaller engineered gene segments that express, or may be adapted to express, proteins, polypeptides, domains, peptides, fusion proteins, and mutants. The nucleic acid may comprise a contiguous nucleic acid sequence of about 5 to about 12000 or more nucleotides, nucleosides, or base pairs.

Encompassed within the definition of "therapeutic nucleic acid" is a "biologically functional equivalent" of a therapeutic nucleic acid that has proved to be of benefit in the treatment or prevention of a disease or health-related condition. Accordingly, sequences that have about 70% to about 99% homology to a known nucleic acid are contemplated in certain aspects.

A. Nucleic Acids Encoding Cytokines

In some embodiments of the pharmaceutical compositions set forth herein the nucleic acid encodes a cytokine. The term "cytokine" is a generic term for proteins released by one cell population which act on another cell as intercellular mediators. The nucleic acid sequences may encode the full length nucleic acid sequence of the cytokine, as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factors (FGFs) such as FGF-α and FGF-β; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-α; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand, FLT-3 or MDA-7.

A non-limiting example of growth factor cytokines involved in wound healing include: epidermal growth factor, platelet-derived growth factor, keratinocyte growth factor, hepatycyte growth factor, transforming growth factors (TGFs) such as TGF-α and TGF-β, and vascular endothelial growth factor (VEGF). These growth factors trigger mitogenic, motogenic and survival pathways utilizing Ras, MAPK, PI-3K/Akt, PLC-gamma and Rho/Rac/actin signaling. Hypoxia activates pro-angiogenic genes (e.g., VEGF, angiopoietins) via HIF, while serum response factor (SRF) is critical for VEGF-induced angiogenesis, re-epithelialization and muscle restoration. EGF, its receptor, HGF and Cox2 are important for epithelial cell proliferation, migration re-epithelializaton and reconstruction of gastric glands. VEGF, angiopoietins, nitric oxide, endothelin and metalloproteinases are important for angiogenesis, vascular remodeling and mucosal regeneration within ulcers (Tarnawski, 2005).

B. Nucleic Acids Encoding Enzymes

Other examples of therapeutic nucleic acids include nucleic acids encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, or a reporter gene.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, glucosyltransferase, HSV thymidine kinase, or human thymidine kinase.

A therapeutic nucleic acid may encode secreted antioxidants (e.g., ascorbic acid or glutathione) or enzymatic antioxidants (e.g., superoxide dismutase (SOD)). SOD, which exists in several isoforms, is a metalloenzyme which detoxifies superoxide radicals to hydrogen peroxide. Two isoforms are intracellular: Cu/Zn-SOD, which is expressed in the cytoplasm, and Mn-SOD, which is expressed in mitochondria (Linchey and Fridovich, 1997). Mn-SOD has been demonstrated to increase resistance to radiation in hematopoetic tumor cell lines transfected with MnSOD cDNA (Suresh et al., 1993). Adenoviral delivery of Cu/Zn-SOD has been demonstrated to protect against ethanol induced liver injury (Wheeler et al., 2001). Additionally adenoviral mediated gene delivery of both Mn-SOD and Cu/Zn-SOD are equally efficient in protection against oxidative stress in a model of warm ischemia-reperfusion (Wheeler et al., 2001).

C. Nucleic Acids Encoding Hormones

Therapeutic nucleic acids also include nucleic acids encoding hormones. Examples include, but are not limited to, growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin 1, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, and thyrotropin releasing hormone.

D. Nucleic Acids Encoding Antibodies

The nucleic acids set forth herein may encode an antibody or fragment thereof. The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

In certain embodiments, the nucleic acid of the pharmaceutical compositions set forth herein encodes a single chain antibody. Single-chain antibodies are described in U.S. Pat. Nos. 4,946,778 and 5,888,773, each of which are hereby incorporated by reference.

E. Diagnostic Nucleic Acids

The exosomes or vesicles in some aspects may include a nucleic acid that is a diagnostic nucleic acid. A "diagnostic nucleic acid" is a nucleic acid that can be applied in the diagnosis of a disease or health-related condition. Also included in the definition of "diagnostic nucleic acid" is a nucleic acid sequence that encodes one or more reporter proteins. A "reporter protein" refers to an amino acid sequence that, when present in a cell or tissue, is detectable and distinguishable from other genetic sequences or encoded polypeptides present in cells. In some embodiments, a therapeutic gene may be fused to the reporter or be produced as a separate protein. For example, the gene of interest and reporter may be induced by separate promoters in separate delivery vehicles by co-transfection (co-infection) or by separate promoters in the same delivery vehicle. In addition, the two genes may be linked to the same promoter by, for example, an internal ribosome entry site, or a bi-directional promoter. Using such techniques, expression of the gene of interest and reporter correlate. Thus, one may gauge the location, amount, and duration of expression of a gene of interest. The gene of interest may, for example, be an anti-cancer gene, such as a tumor suppressor gene or pro-apoptotic gene.

Because cells can be transfected with reporter genes, the reporter may be used to follow cell trafficking. For example, in vitro, specific cells may be transfected with a reporter and then returned to an animal to assess homing. In an experimental autoimmune encephalomyelitis model for multiple sclerosis, Costa et al. (2001) transferred myelin basic protein-specific CD4+ T cells that were transduced to express IL-12 p40 and luciferase. In vivo, luciferase was used to demonstrate trafficking to the central nervous system. In addition, IL-12 p40 inhibited inflammation. In another system, using positron emission tomography (PET), Koehne et al. (2003) demonstrated in vivo that Epstein-Barr virus (EBV)-specific T cells expressing herpes simplex virus-1 thymidine kinase (HSV-TK) selectively traffic to EBV+ tumors expressing the T cells' restricting HLA allele. Furthermore, these T cells retain their capacity to eliminate targeted tumors. Capitalizing on sequential imaging, Dubey et al. (2003) demonstrated antigen specific localization of T cells expressing HSV-TK to tumors induced by murine sarcoma virus/Moloney murine leukemia virus (M-MSV/M-MuLV). Tissue specific promoters may also be used to assess differentiation, for example, a stem cell differentiating or fusing with a liver cell and taking up the characteristics of the differentiated cell such as activation of the surfactant promoter in type II pneumocytes.

Preferably, a reporter sequence encodes a protein that is readily detectable either by its presence, its association with a detectable moiety or by its activity that results in the generation of a detectable signal. In certain aspects, a detectable moiety may include a radionuclide, a fluorophore, a luminophore, a microparticle, a microsphere, an enzyme, an enzyme substrate, a polypeptide, a polynucleotide, a nanoparticle, and/or a nanosphere, all of which may be coupled to an antibody or a ligand that recognizes and/or interacts with a reporter.

In various embodiments, a nucleic acid sequence of the invention comprises a reporter nucleic acid sequence or encodes a product that gives rise to a detectable polypeptide. A reporter protein is capable of directly or indirectly generating a detectable signal. Generally, although not necessarily, the reporter gene includes a nucleic acid sequence and/or encodes a detectable polypeptide that are not otherwise produced by the cells. Many reporter genes have been described, and some are commercially available for the study of gene regulation (e.g., Alam and Cook, 1990, the disclosure of which is incorporated herein by reference). Signals that may be detected include, but are not limited to color, fluorescence, luminescence, isotopic or radioisotopic signals, cell surface tags, cell viability, relief of a cell nutritional requirement, cell growth and drug resistance. Reporter sequences include, but are not limited to, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, G-protein coupled receptors (GPCRs), somatostatin receptors, CD2, CD4, CD8, the influenza hemagglutinin protein, symporters (such as NIS) and others well known in the art, to which high affinity antibodies or ligands directed thereto exist or can be produced by conventional means, and fusion proteins comprising a membrane bound protein appropriately fused to an antigen tag domain from, among others, hemagglutinin or Myc. Kundra et al., 2002, demonstrated noninvasive monitoring of somatostatin receptor type 2 chimeric gene transfer in vitro and in vivo using biodistribution studies and gamma camera imaging.

In some embodiments, a reporter sequence encodes a fluorescent protein. Examples of fluorescent proteins which may be used in accord with the invention include green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED). It is to be understood that these examples of fluorescent proteins is not exclusive and may encompass later developed fluorescent proteins, such as any fluorescent protein within the infrared, visible or ultraviolet spectra.

In various embodiments, the desired level of expression of at least one of the reporter sequence is an increase, a decrease, or no change in the level of expression of the reporter sequence as compared to the basal transcription level of the diagnostic nucleic acid. In a particular embodiment, the desired level of expression of one of the reporter sequences is an increase in the level of expression of the reporter sequence as compared to the basal transcription level of the reporter sequence.

In various embodiments, the reporter sequence encodes unique detectable proteins which can be analyzed independently, simultaneously, or independently and simultaneously. In other embodiments, the host cell may be a eukaryotic cell or a prokaryotic cell. Exemplary eukaryotic cells include yeast and mammalian cells. Mammalian cells include human cells and various cells displaying a pathologic phenotype, such as cancer cells.

For example, some reporter proteins induce color changes in cells that can be readily observed under visible and/or ultraviolet light. The reporter protein can be any reporter protein known to those of ordinary skill in the art. Examples include GFP, RFP, BFP and luciferase.

Nucleic acids encoding reporter proteins include DNAs, cRNAs, mRNAs, and subsequences thereof encoding active fragments of the respective reporter amino acid sequence, as well as vectors comprising these sequences.

Exemplary methods of imaging of reporter proteins include gamma camera imaging, CT, MRI, PET, SPECT, optical imaging, and ultrasound. In some embodiments, the diagnostic nucleic acid is suitable for imaging using more than one modality, such as CT and MRI, PET and SPECT, and so forth.

Additional information pertaining to examples of reporters in imaging are set forth in Kumar, 2005; Kundra et al., 2005; and Kundra et al., 2002, each of which is herein specifically incorporated by reference in its entirety.

VII. Pharmaceutical Compositions

In certain aspects, the compositions or agents for use in the methods are suitably contained in a pharmaceutically acceptable carrier. The carrier is non-toxic, biocompatible and is selected so as not to detrimentally affect the biological activity of the agent. The agents in some aspects of the invention may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the invention also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain less, than, equal to, or more than 10 mg, 25 mg, 50 mg or up to about 100 mg of human scrum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-fungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VIII. Kits

Some embodiments concern kits, such as diagnostic and therapeutic kits, as well as kits for preparing and/or delivering exosomes. For example, a kit may comprise one or more pharmaceutical compositions as described herein and optionally instructions for their use. Kits may also comprise one or more devices for accomplishing administration of such compositions. For example, a subject kit may comprise a pharmaceutical composition and catheter for accomplishing direct administration of the composition to a patient having or at risk for a demyelination disorder. In other embodiments, a subject kit may comprise pre-filled ampoules of isolated exosomes, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. In some embodiments, kits will comprise the container described above and one or more other containers comprising materials desirable from a commercial and user standpoint, including buffers, diluents, filters, needles, syringes, and package inserts with instructions for use.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Environmental Enrichment

Figures 2A, 2B, 2C:
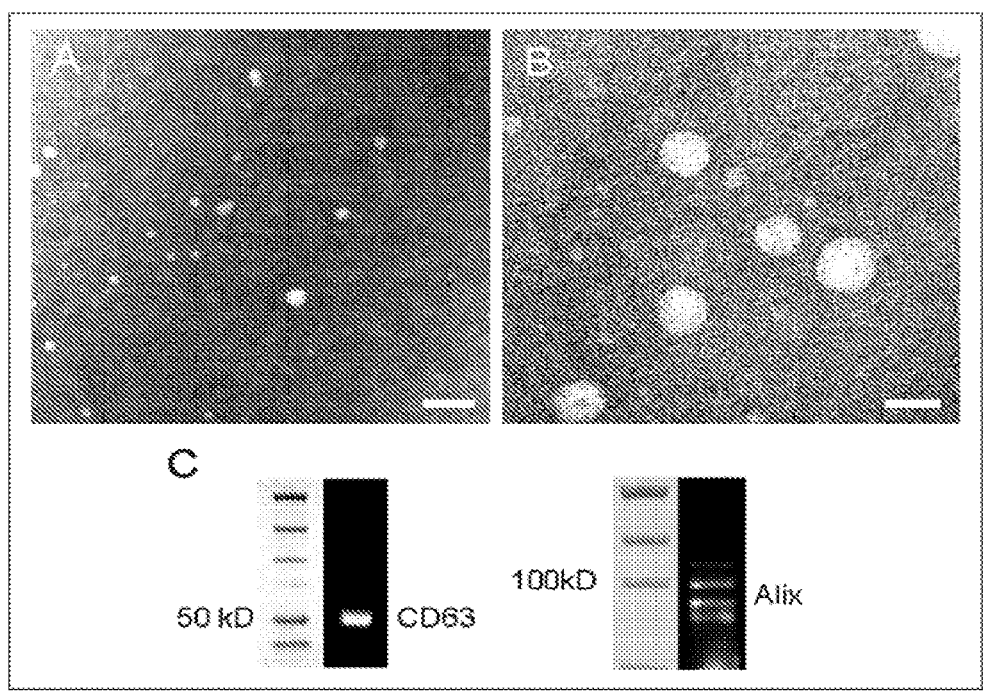
FIGS. 2A-2C. Confirmation of exosome recovery from serum. Electron microscopy images of serum-exosomes at low (A) and high (B) power. Scale bars=200 (A) and 100 (B) nm. Western blots (C) show presence two well-characterized exosomal protein markers: CD63 and Alix.

The inventors established a Marlau-style EE cage for rats to test whether exosomes (FIG. 1) derived from peripheral blood (FIGS. 2A-2C) of EE-exposed (FIGS. 7A-7F) rats could reduce OS and promote myelination compared to non-enriched (NE) counterparts.

Figures 3A, 3B, 3C:
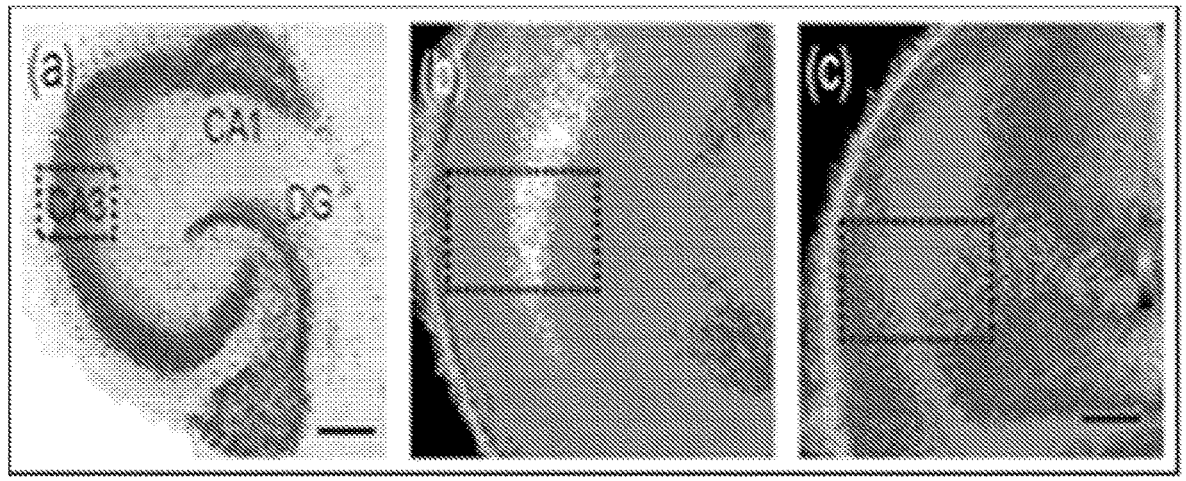
FIGS. 3A-3C. Semi-quantitative analysis of OS in hippocampal slice cultures from exposure to interferon gamma (IFN-$\gamma$). (A) NeuN immunohistochemical labeling of a hippocampal slice cultures, for cytoarchitectural reference and to chow the CA3 area of interest (dotted line box) used for quantification of OS via CellROX™, a fluorogenic marker of OS (Grinberg, Y Y, et al. (2012), J Neurochem. 122:221-9). (B-C) Representative CellROX™-labeled images show IFN-$\gamma$ exposure (500 U/mL×7 hours) significantly ($p<0.02$; n=3/group) increased OS (B) compared to control (C). Scale bar=200 µm. Slice cultures were prepared and maintained as previously described (Grinberg, et al., 2012; Mitchell, et al., 2011; Pusic, et al., 2011).

EE also generates low-level increased production of reactive oxygen species that trigger increased production of anti-oxidants. Accordingly, EE triggers a net reduction in brain OS. As a result, the inventors tested whether exosomes derived from the blood (FIGS. 2A-2C) of animals that received EE (FIGS. 7A-7F), when compared to NE counterparts, could recapitulate this effect when applied to hippocampal slice cultures. OS was induced by menadione exposure (FIGS. 3A-3B). These results confirm that exosomes from EE, but not NE animals, significantly reduced brain tissue OS when measured three days after exosome exposure. Furthermore, this decreased OS is not observed when exosomes are exposed to UV light prior to administration, suggesting that their effects were mediated by RNA species. Specific values were: Control: $1.00\pm0.071$; EE: $0.55\pm0.03$ ($p\leq0.001$); NE: $0.95\pm0.08$; EE+UV: $0.99\pm0.05$ (n=6-18/group). Further demonstration of reduction of brain OS by application of EE exosomes is in FIGS. 18A-18D.

Since EE mitigates cognitive decline from aging (Ahlskog, et al., 2011), which occurs with increased OS (Sohal & Weindruch, 1996), and anti-oxidants promote myelination (Podratz, et al., 2004), the inventors hypothesized that EE-derived exosomes could increase brain myelin content. Accordingly, the inventors measured MBP content in hippocampal slice cultures exposed to exosomes and found that after three days, MBP was significantly increased after exposure to EE- but not NE-derived exosomes or controls. Furthermore, this effect of EE exosomes could be abrogated by exposure to UV light, again suggesting that RNA species mediate these effects. Specific values were: Control: $1.00\pm0.08$; EE: $1.47\pm0.09$ ($p\leq0.001$); NE: $1.01\pm0.19$; EE+UV: $0.81\pm0.02$ (n=3-5/group).

In the above EE experiments, adult animals were used. The inventors hypothesized that exosomes of EE exposed aging rats (>500 g), could also improve myelinating capacity of brain tissue. The inventors found that exosomes from aging EE (FIGS. 7A-7F) but not aging NE rats increased the number of differentiating OPCs (quantified via immunostaining for pre-oligodendrocyte marker O4) in hippocampal slice cultures. Specific values were: Control: $1.00\pm0.23$; Aging-EE: $2.95\pm0.54$; Aging-NE: $1.36\pm0.13$ (n=3-5/group). In another experiment, treatment with young, young-EE and aging-EE exosomes significantly (*$p\leq0.001$; n=6-19/group) increased O4+ fluorescence intensity compared to baseline and slices treated with aging, NE and aging-NE exosomes. (FIG. 13C) Exposure of exosomes to 254 nm ultraviolet light for one hour before application to slices eliminated this increase.

Similarly, OS was significantly ($p\leq0.001$) reduced in naïve slice cultures by treatment for three hours with aging-EE-derived exosomes compared to their NE counterparts derived from aging animals. As above, this significant reduction in OS was abrogated by pretreatment of EE-exosomes with ultraviolet light. Specific values were: Control: $1.00\pm0.06$; aging-EE: $0.81\pm0.04$; aging-NE: $1.21\pm0.02$; aging-EE+UV: $1.22\pm0.05$ (n=6-9/group). Interestingly, aging-NE exposed cultures showed a significant (p=0.001) increase in OS compared to control, supporting the notion that aging is associated with pro-inflammatory change, which can promote demyelination.

Figures 13A, 13B, 13C, 13D:
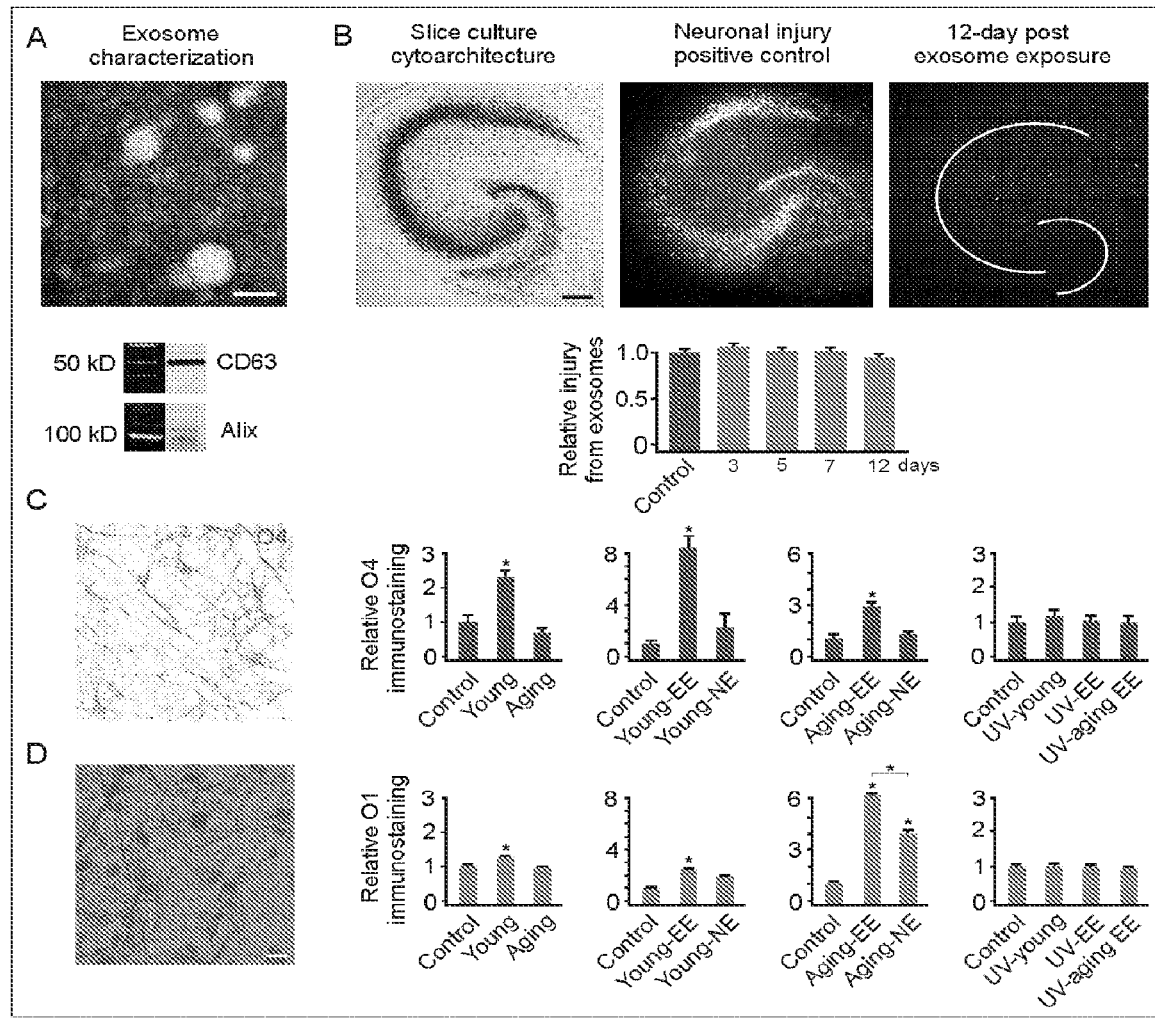
FIGS. 13A-13D. Exosomes derived from serum were non-toxic and increased pre-oligodendrocyte levels. (A) Exosome isolation from serum was confirmed by electron microscopy and Western blot for surface markers CD63 and Alix. Scale bar=40 nm. (B) Exosome application to hippocampal slice cultures was non-toxic. Exosomes were resuspended in PBS and applied to 21 days in vitro slice cultures. Slices were then stained with Sytox, a fluorescent marker of cell death, at 3, 5, 7 and 12 days post-treatment. NeuN immunostaining image (left) is shown to illustrate neuronal architecture. Sytox positive image (center) shows control with neuronal injury induced by 24 hour exposure to 20 µM N-methyl-d-aspartate. Quantification of Sytox intensity (n=9/group) confirmed that exosome application caused no significant injury (right). Scale bar=250 µm. (C) Exemplary confocal image (left) of O4 positive cells in nutritive exosome-treated slice culture. Scale bar=25 µm. Low power images were used for quantification of staining intensity from a stereotypic area of interest in CA3. Treatment with young, young-EE and aging-EE exosomes significantly (*p≤0.001; n=6-19/group) increased O4+ fluorescence intensity of baseline and slices treated with aging, NE and aging-NE exosomes. Exposure of exosomes to 254 nm ultraviolet (UV) light for one hour before application to slices eliminated this increase. (D) Exemplary confocal image (left) of O1 positive cells in nutritive exosome-treated slice culture. Scale bar=25 µm. As before, quantification of low power images revealed significantly (*p≤0.001; n=6-19/group) increased O1+ fluorescence intensity in nutritive exosome-treated slices compared to control and non-nutritive exosome-treated slices. Once again, exosomes exposed to UV light lost their effect, indicating that the responsible factor is an RNA species. Significance was determined by ANOVA plus post hoc Holm-Sidak testing.

To demonstrate that exosome treatment of hippocampal slice cultures was non-toxic, exosomes were resuspended in PBS and applied to 21 days in vitro slice cultures. Slices were then stained with Sytox, a fluorescent marker of cell death, at 3, 5, 7 and 12 days post-treatment. NeuN immunostaining (FIG. 13B left) is shown to illustrate neuronal architecture. Sytox positive image (FIG. 13B center) shows control with neuronal injury induced by 24 hour exposure to 20 µM N-methyl-d-aspartate. Quantification of Sytox intensity (n=9/group) confirmed that exosome application caused no significant injury (FIG. 13B right).

Example 2: Exosomes from Young/Aging Rats

Cognitive decline from aging occurs with increased OS (Sohal & Weindruch, 1996) and the systemic milieu of young animals can rejuvenate aspects of the aged CNS (Ruckh, et al., 2012). Accordingly, the authors hypothesized that exosomes from young animals could mitigate OS (FIGS. 3A-3C), a critical aspect of cellular aging. Indeed, the authors found that exosomes from the blood of young but not aging rats significantly ($p\leq0.001$) decreased OS in hippocampal slice cultures. Furthermore, this nutritive effect of young exosomes could be abrogated by exposing exosomes to UV light, suggesting that RNA species within young exosomes are responsible. Specific values were: Control: 1.00±0.1; Young: 0.59±0.04 (p≤0.001); Aging: 0.90±0.09; Young+UV: 0.95±0.05; (n=9/group).

Since exosomes could stimulate increased myelin content (MBP), the inventors hypothesized that that exosomes could affect the OPC pool of brain tissue. Exosomes derived from the blood of young and old rats were applied to hippocampal slices as described above. OPC differentiation (quantified via immunostaining for oligodendrocyte precursor marker O4) was significantly (p≤0.001) increased in tissue exposed to exosomes from young but not aged animals. Again, this effect of 'young' exosomes could be abrogated by UV light, suggesting RNA species are responsible for the increased OPC pool. Specific values were: Control: 1.00±0.22; Young: 2.36±0.25; Aging: 0.69±0.14; Young+UV: 1.21±0.43 (n=7-9/group).

As described above, the inventors described that exosomes from EE-stimulated animals could improve myelin content. The inventors hypothesized that EE may be rejuvenating animals. Accordingly, the inventors tested whether exosomes from the blood of young animals had a similar effect on brain myelin as exosomes from aging EE-stimulated animals. Indeed, MBP (quantified via Western blot) was significantly (p<0.05) increased in hippocampal slices exposed to exosomes from young but not aging animal serum. Furthermore, while young exosomes already significantly increased MBP levels following 3-day exposure, this effect improved further following 7-day exposure to young exosomes. Specific values for 3-day exposure were: Control: 1.00±0.10; Young: 1.56±0.22; Aging: 0.86±0.08.

Specific values for 7-day significant (p≤0.01) increases in MBP were: Control: 1.00±0.07; Young: 1.95±0.15; Aging: 0.86±0.08; n=4-6/group. Collectively, these data indicate that young exosomes promote myelination and may do so through mRNA and/or miRNA signaling.

Figures 14A, 14B, 14C, 14D:
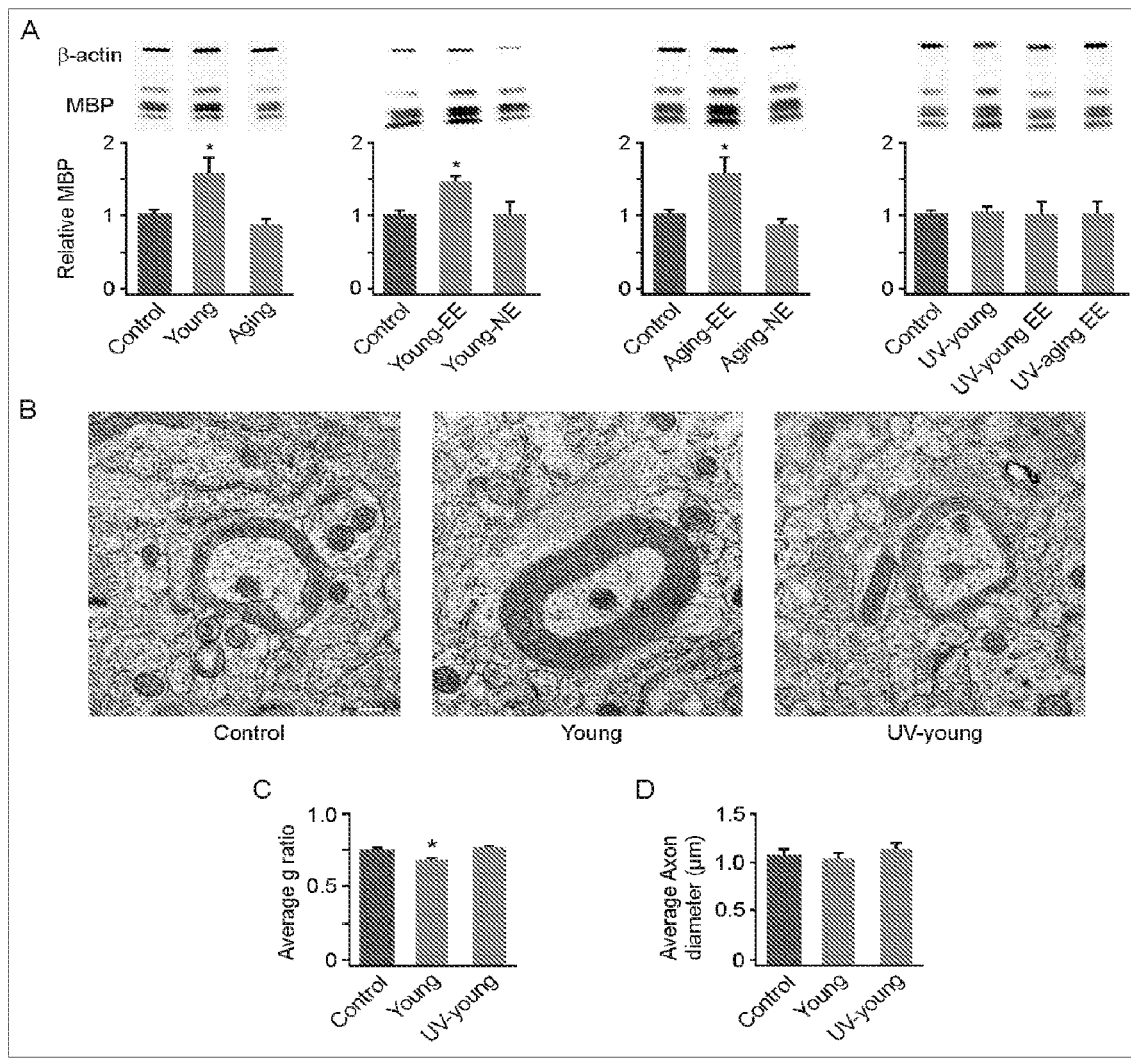
FIGS. 14A-14D. Young and environmentally enriched exosomes enhanced myelination. (A) Nutritive exosomes enhanced baseline slice culture myelin levels. Slice cultures were treated with exosomes and harvested three days later for Western blot analysis of myelin basic protein (MBP) content. Young, young environmentally enriched (young-EE), and aging environmentally enriched (aging-EE) rat serum-derived exosomes (n=3-18) all significantly (*p=0.004, 0.008, and 0.003, respectively) increased MBP content of slice cultures above control, whereas their aging, non-enriched (NE) and aging non-enriched (aging-NE) counterparts did not. Exposure of exosomes to 254 nm UV light for one hour before application to slices ablated their effect. (B) Representative electron micrograph images show myelin thickness in control cultures (left) and three days after exposure to young serum-derived (middle) or UV-exposed exosomes (right). Scale bar=200 nm. (C) g ratio (axon diameter/fiber diameter) calculation (n=3/group, with 20-27 axons measured per group) revealed a significant (*p<0.001) decrease in young exosome-treated versus control and UV-exosome treated samples, indicating improved myelin thickness. (D) Axon diameter was not significantly different in young exosome-treated versus control and UV-exosome treated samples (n=3/group, with 20-27 axons measured per group). Significance was determined by ANOVA plus post hoc Holm-Sidak testing.

As further demonstration that both young and environmentally enriched exosomes enhance myelination, slice cultures treated with young, young environmentally enriched (young-EE), and aging environmentally enriched (aging-EE) rat serum-derived exosomes (n=3-18) all displayed significantly (*p=0.004, 0.008, and 0.003, respectively) increased MBP content above control, as shown by Western blot (FIG. 14A). In contrast, slice cultures treated with aging, non-enriched (NE) and aging non-enriched (aging-NE) exosomes did not display increased MBP content (FIG. 14A). Exposure of exosomes to 254 nm UV light for one hour before application to slices ablated their effect. The effect of young exosomes in increasing myelination is also demonstrated by electron micrographs showing enhanced thickness of the myelin sheath (FIGS. 14B-14D).

Figures 8A, 8B, 8C, 8D, 8E:
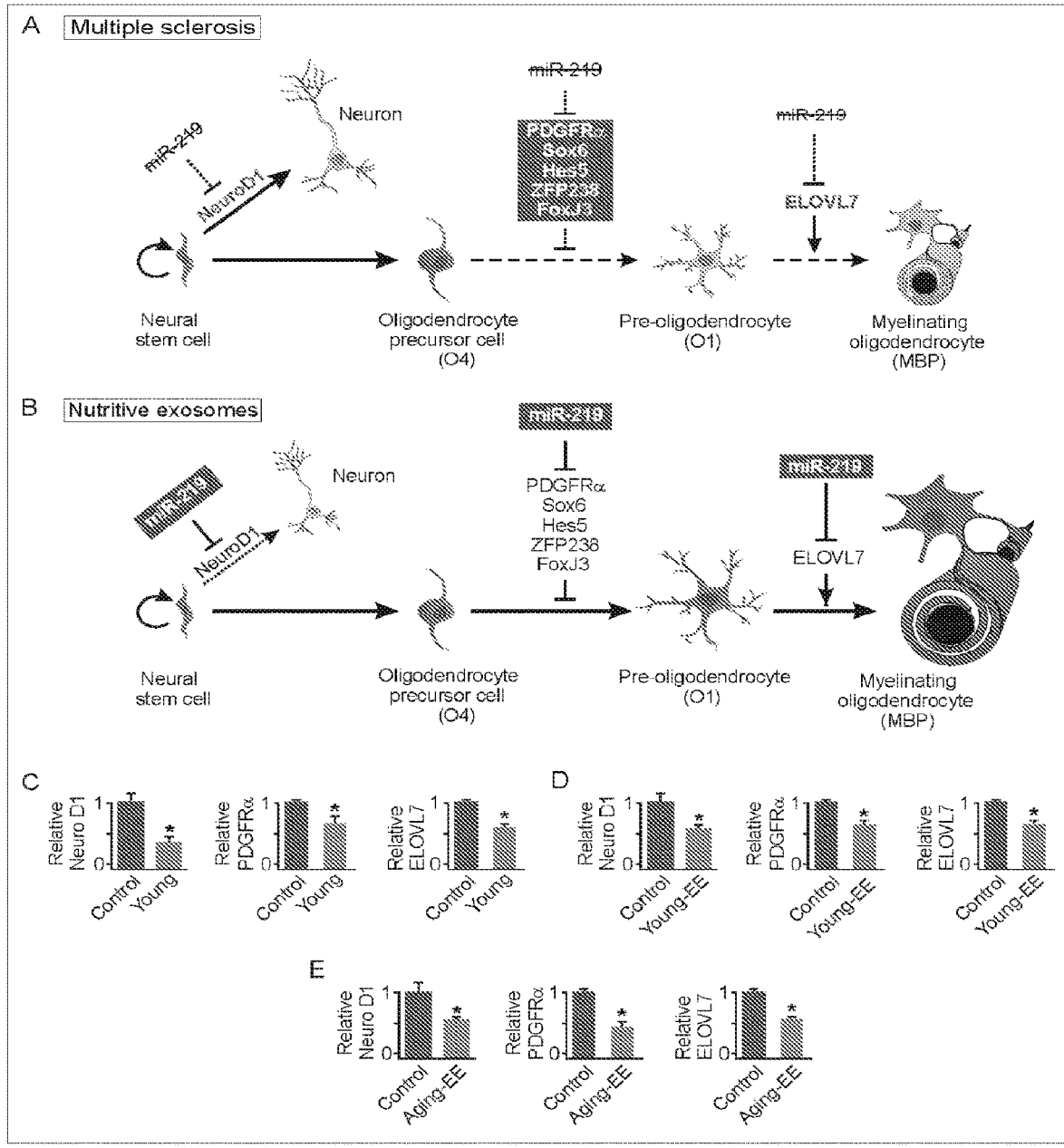
FIGS. 8A-8E. Young and environmentally enriched exosomes deliver functional miR-219 that impacts oligodendrocyte differentiation and myelination. Schematic illustration of the involvement of miR-219 in oligodendrocyte differentiation. (A) In multiple sclerosis oligodendrocyte precursor cells are actively prevented from differentiating into myelin producing cells in part due to deficiency of miR-219. (B) However, upon exposure to nutritive exosomes, neural stem cells preferentially enter the oligodendrocyte lineage due to inhibition of the proneurogenic factor NeuroD1. miR-219 also suppresses expression of a number of other factors that inhibit OPC differentiation, such as PDGFR$\alpha$, a receptor for a mitogenic factor that promotes proliferation and prohibits differentiation. Finally, miR-219 decreases levels of ELOVL7, a regulator of lipid metabolism whose over-activity could lead to demyelination. (C-E) One day after application, nutritive exosome-treated naïve slice cultures (n=3-10/group) expressed significantly (*) less NeuroD1, PDGFR$\alpha$ and ELOVL7 (p value ranges of 0.04-0.002, 0.03-0.003, and 0.02-0.001, for C, D, and E, respectively) relative to levels in untreated control slices. Significance determined by Student's t test.
Figure 15:
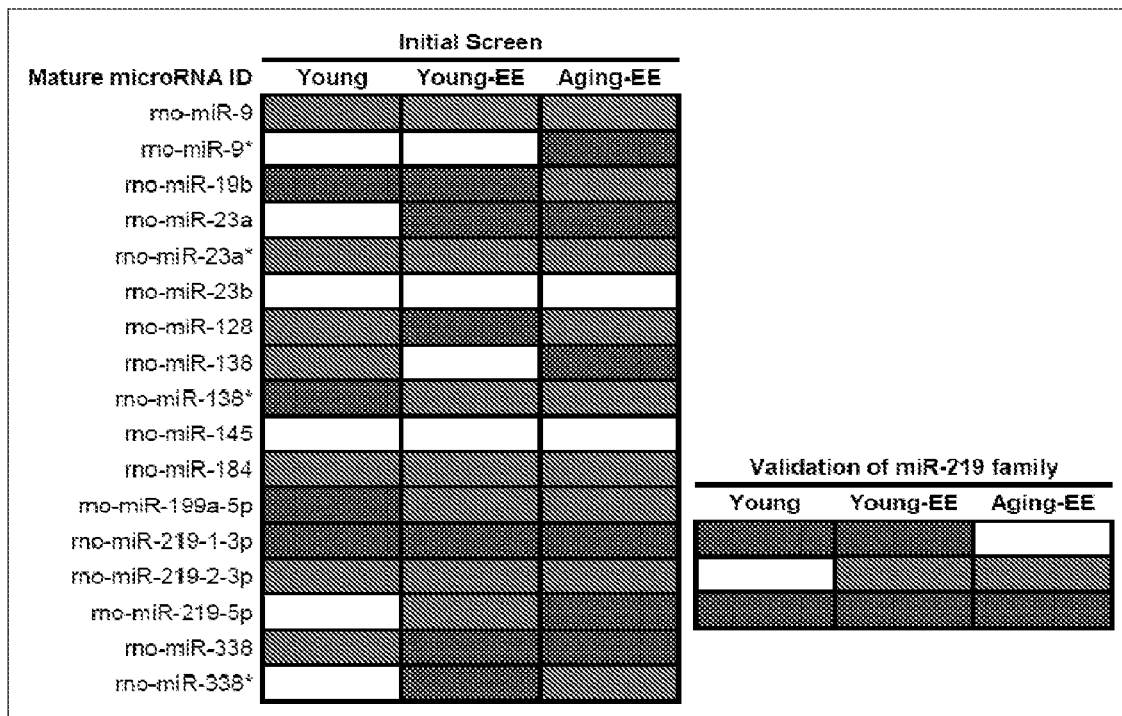
FIG. 15. Young and environmentally enriched exosomes were enriched in miRNAs necessary for oligodendrocyte differentiation. miRNA content of young, young-EE and aging-EE exosomes were compared to aging-NE exosomal miRNA utilizing two different methods: (A) SBI's Rat Genome-wide microRNA qPCR Array Panel, and (B) TaqMan Array Rodent MicroRNA Cards. Mature species that were significantly (i.e., ≥2 fold, n=2-3) enriched in each class of exosomes are shown in dark grey. miRNAs that were readily detectable but not significantly enriched are shown in white. miRNAs that could not be detected are shown in grey. † TaqMan microarray cards contained mmu-miR-219, which likely cross-reacted with rno-miR-219 species due to high sequence homology.

Given the increasing evidence that miRNAs are involved in the pathogenesis of demyelination from neurodegenerative disorders such as MS, the inventors next screened for differences in miRNA content of young and aging animal serum-derived exosomes. Levels of 21 microRNAs previously implicated in OPC maturation were assayed in exosomes derived from scrum of young or aging animals. Both groups were positive for 10 microRNAs (miR-9, miR-19b. miR-23a, miR-23b, miR-128, miR-138, miR-145, miR-199a-5p, miR-219, miR-338, and miR-138). Specific microRNAs (miR-219, miR-138, miR-338, and miR-199a-5p) were enriched in young exosomes. The inventors plan to focus on miR-219, as it showed the most significant enrichment, and is known to affect multiple steps of OPC differentiation into mature, myelinating oligodendrocytes (FIG. 8A). Results of experiments showing enrichment of miRNAs necessary for oligodendrocyte differentiation in young and environmentally enriched exosomes are shown in FIG. 15. Furthermore, FIGS. 8C-8E show the changes in protein expression levels of mRNAs targeted by miR-219 (FIG. 8B) in slice cultures one day after application of nutritive (that is, myelin promoting and oxidative stress reducing) exosomes.

Example 3: Remyelination Using Young Exosomes

Figures 9A, 9B:
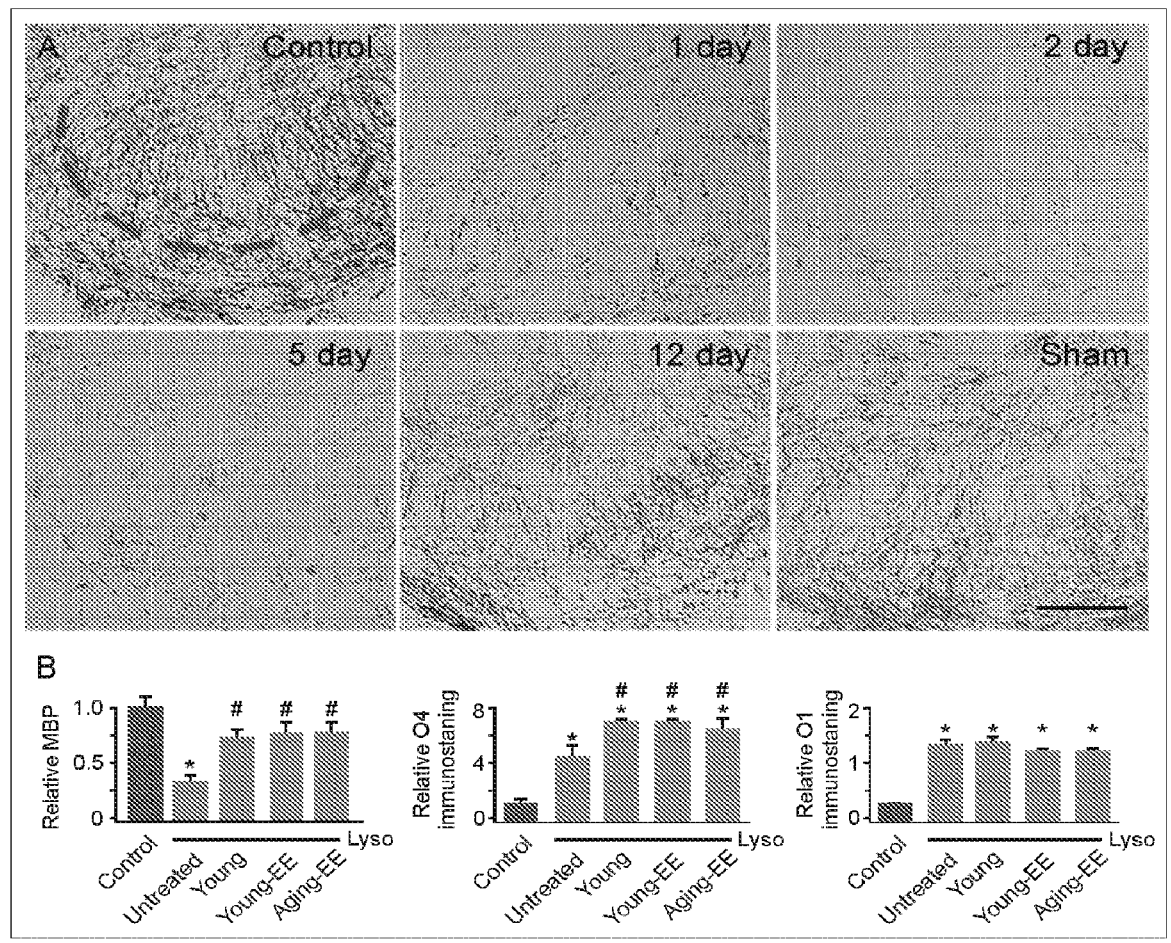
FIGS. 9A-9B. Young and environmentally enriched exosomes improved recovery from demyelinating injury. (A) Lysolecithin (0.5 mg/mL) exposure for 17 hours was used as a means to evoke demyelination followed by remyelination in slice cultures. Timecourse of recovery was determined via staining for myelin basic protein (MBP). Control slice shows typical MBP immunostaining in a healthy, mature slice culture. Lysolecithin induced demyelination that peaked at two days, showed first signs of recovery at five days, and progressively returned to normal by twelve days. Sham treatment (17 hour exposure to fresh media without lysolecithin) had no injurious effect on myelin content and/or distribution. Scale bar=200 µm. (B) Immediately after exposure to lysolecithin, cultures were treated with exosomes derived from young, young-EE, or aging-EE animals. Five days later, at the onset of remyelination, cultures were collected and MBP content analyzed via Western blot. While lysolecithin (Lyso) exposure triggered a significant (*p<0.001; n=6-16) reduction of MBP in all groups compared to control, exosome exposure prompted a significant (#p<0.001) increase in remyelination compared to that seen with lysolecithin alone. Similarly, slice cultures collected 5 days after lysolecithin treatment also revealed significantly (*p<0.001; n=4-8/group) increased presence of O4 positive cells. All exosome treatments significantly enhanced O4 staining (#p<0.001) above that seen with lysolecithin treatment alone. While O1 staining also significantly increased (*p<0.001; n=3-4/group) 5 days after lysolecithin treatment, no additional increase was seen with exosome treatment, suggesting that exosomes may directly increase remyelination by surviving mature oligodendrocytes. Significance was determined by ANOVA plus post hoc Holm-Sidak testing.

The inventors next hypothesized that young exosomes, which can improve baseline myelin content in healthy tissue, can also improve remyelination following an experimental model of demyelination. Indeed, the inventors demonstrated that young, young-EE and aging-EE exosomes significantly (p≤0.001) improved recovery following acute demyelination induced by transient exposure to lysolecithin (FIGS. 9A-9B). Immediately after exposure to lysolecithin, cultures were treated with exosomes derived from young, young-EE, or aging-EE animals. Five days later, at the onset of remyelination, cultures were collected and MBP content analyzed via Western blot (FIG. 9B). While lysolecithin (Lyso) exposure triggered a significant (*p<0.001; n=6-16) reduction of MBP in all groups compared to control, exosome exposure prompted a significant (#p<0.001) increase in remyelination compared to that seen with lysolecithin alone. Similarly, slice cultures collected 5 days after lysolecithin treatment also revealed significantly (*p<0.001; n=4-8/group) increased presence of O4 positive cells. All exosome treatments significantly enhanced O4 staining (#p<0.001) above that seen with lysolecithin treatment alone. While O1 staining also significantly increased (*p<0.001; n=3-4/group) 5 days after lysolecithin treatment, no additional increase was seen with exosome treatment, suggesting that exosomes may directly increase remyelination by surviving mature oligodendrocytes. Significance was determined by ANOVA plus post hoc Holm-Sidak testing.

Example 4: IFNγ-Stimulated Dendritic Cell-Derived Exosomes

The inventors studied dendritic cell-derived exosomes. Exosomes do not contain a random sampling of their parent cell's cytoplasm, but are enriched in specific mRNA, miRNA, and protein (Brobrie, et al., 2011). This cargo is protected from degradation by proteases and RNases while the vesicle is in the interstitial space, and retains bioactivity once taken up by a recipient cell. Thus, they facilitate transfer of signaling and enzymatic activities that would otherwise be restricted to individual cells based on gene expression (Lee, et al., 2011). Recent work shows that immune cells exposed to OS release exosomes that convey increased resistance against OS to neighboring cells (Eldh, et al., 2010). Importantly, this effect is seen two hours after exposure, implying rapid translation of exosomal mRNA to protective proteins (Eldh, et al., 2010), most likely antioxidants or production of oxidant/antioxidant system related miRNAs.

Exosomes were isolated from rat hippocampal slice culture conditioned media and blood using ExoQuick-TC™ isolation kits. Interferon gamma (IFNγ) was used as an initial stimulus because of evidence suggesting that T cells (and their production of IFNγ) are involved in EE-based neuroprotection. Exposure to IFNγ was non-injurious, but triggered a significant (p<0.02; n=3/group) increase in OS from 1.00±0.07 to 1.50±0.27 in the CA3 region of the slices, as measured via CellROX™, a fixable marker of reactive oxygen species.

Next, the inventors exposed hippocampal brain slices to a physiological dose of IFNγ and harvested exosomes from conditioned media three days later (conditioned media from slices exposed to media alone were collected for control). Then, new slices were treated with these exosomes for three hours, before exposure to OS via mitochondrial inhibition (menadione), and measured OS via CellROX™. This treatment with exosomes from IFNγ stimulated cultures triggered a significant ($p<0.002$; n=3/group) protection from OS, from 1.00±0.06 to 0.63±0.05. Thus, like immune cells (Eldh M et al. (2010) PLoS ONE), neural cells (microglia) exposed to OS can transfer increased resilience to OS via exosomes.

Next the inventors isolated exosomes from the blood of young and aging rats. When applied to slice cultures (n=9/group) for a day, they found that exosomes from young rats triggered a significant ($p<0.001$) reduction (0.59±0.04) in OS compared to control, young-UV treated, and aging exosomes (1.00±0.1, 0.95±0.05, and 0.90±0.10, respectively).

Furthermore, exosomes from young rat blood triggered a significant ($p=0.01$; n=3/group) increase in OPC differentiation. Accordingly, serum-derived exosomes seem well-suited for development as a therapeutic to promote myelination.

The inventors stimulated brain slice cultures with 500 U/mL of IFN-γ, then harvested released exosomes. They chose IFNγ as the stress inducing signal since acute IFNγ exposure triggers a significant ($p<0.02$; n=3/group) rise of OS in the CA3 hippocampal region [Note: $p<0.05$ (*); $p≤0.01$ (); $p≤0.001$ (*)]: Control 1.00±0.07; IFNγ 1.50±0.27*.

When IFNγ was applied phasically (i.e., every 12 hours for seven days), OS was significantly (n=5/group) reduced: Control 1.00±0.07; IFNγ 0.54±0.12***. Furthermore, these slice culture-IFNγ stimulated exosomes significantly reduced susceptibility to spreading depression (SD), the most likely cause of migraine. Thus, like peripheral immune cells, neural cells (microglia) exposed to OS transfer increased resilience to OS via exosomes. The inventors went on to show that nasal administration of IFNγ also reduces susceptibility to neocortical SD in vivo.

Notably, the above work also shows (data not described) that IFNγ stimulated slice culture exosomes increase tissue MBP when applied to separate slice cultures. Ruckh J and coworkers (2012) show that remyelination after experimentally induced demyelination in aged animals could be rejuvenated by exposure to the systemic milieu (i.e., blood) of younger counterparts. The inventors showed this "systemic milieu" effect involves exosomes from serum that reduce OS, increase OPC differentiation and increase production of MBP. Specifically, comparisons of exosomes from young vs. aging rats (when applied to rat slice cultures) show that: OS was significantly reduced (n=9/group) by exposure to "young vs. aging-derived" exosomes, an effect the inventors tested for involvement of mRNA or miRNA by destroying these signaling molecules via exposure to UV light: Control 1.00±0.1; Young 0.59±0.04***; Aging 0.90±0.09; Young±UV 0.95+0.05. These data suggests that an RNA species in responsible for the reduction in OS. Measurements were made using CellROX™.

OPC differentiation was significantly increased (n=7-9/group) by exposure to young vs. aging-derived exosomes, an effect removed by UV exposure of young exosomes:

| | |
|---|---|
| Control | 1.00 ± 0.22 |
| Young | 2.36 ± 0.25 *** |
| Aging | 0.69 ± 0.14 |
| Young + UV | 1.21 ± 0.43. |

These data also suggest that an RNA species is contained within young exosomes that promotes OPC differentiation. Measurements were made using semi-quantitative immunostaining.

Slice culture MBP content was significantly increased by exposure to young vs. aging-derived exosomes, effects removed by UV exposure of young exosomes:

| | | |
|---|---|---|
| 3 hr: | Control | 1.00 ± 0.03 |
| | Young | 0.85 ± 0.09 |
| | Aging | 0.47 ± 0.07 |
| | Young + UV | 0.62 ± 0.16 (n = 3-6/group). |
| 1 day: | Control | 1.00 ± 0.03 |
| | Young | 1.05 ± 0.12 |
| | Aging | 0.53 ± 0.08 ** |
| | Young + UV | 0.62 ± 0.16 (n = 3-6/group). |

These two sets (i.e., 3 hr and 1 day) of data suggest that "aging" exosomes (and young exosomes exposed to UV) contain signaling factors that can impede myelination.

| | | |
|---|---|---|
| 3 day: | Control | 1.00v ± 0.10 |
| | Young | 1.56 ± 0.22 * |
| | Aging | 0.86 ± 0.08 (n = 4-6/group). |
| 7 day: | Control | 1.00 ± 0.07 |
| | Young | 1.95 ± 0.15 ** |
| | Aging | 0.86 ± 0.0.08 (n = 4/group). |

Collectively, these data indicate that young exosomes promote myelination and may do so through mRNA and/or miRNA signaling. MBP was quantified via Western blot.

Given the increasing evidence that miRNAs are involved in the pathogenesis of demyelination from neurodegenerative disorders such as multiple sclerosis, the inventors next screened for miRNA expression differences between young and aging exosomes. Levels of 21 microRNAs previously implicated in OPC maturation were assayed in exosomes derived from serum of young or aging animals.

Both groups were positive for 10 microRNAs (miR-9, miR-19b, miR-23a, miR-23b, miR-128, miR-138, miR-145, miR-199a-5p, miR-219, miR-338, and miR-138). Specific microRNAs (miR-219, miR-138 and miR-199a-5p) were selectively enriched in young exosomes.

miR-219 will be emphasized, as it showed the most significant enrichment, and is known to affect multiple steps of OPC differentiation into mature, myelinating oligodendrocytes. Results of a further experiment showing enrichment of miRNAs necessary for oligodendrocyte differentiation in young and environmentally enriched exosomes are shown in FIG. 15. Furthermore, FIGS. 8C-8E show the changes in protein expression of mRNAs targeted by miR-219 (FIG. 8B) in slice cultures one day after application of nutritive exosomes.

The inventors next demonstrated that young exosomes significantly improved remyelination following acute demyelination produced by transient exposure to lysolecithin. For example, the inventors used 17 h exposure to lysolecithin to show that slice cultures transiently reduce their myelin content by about 80%.

As determined by Western blot quantification of MBP levels, exposure to young exosomes provided a significantly improved recovery from lysolecithin-induced demyelination at 5 days (n=5-6).

| | |
|---|---|
| Control | 1.00 ± 0.11 |
| Lyso | 0.34 ± 0.04 |
| Lyso + Young | 0.73 ± 0.08 ** |

Environmental enrichment [(EE); i.e., volitionally increased social, intellectual, and physical activity] also generates low-level increases in reactive oxygen species that trigger increased production of anti-oxidants. Accordingly, EE triggers a net reduction in brain OS. As a result, the inventors tested whether exosomes derived from the serum of animals that received EE versus those that experienced normal animal housing [i.e., non-enriched (NE)] showed comparisons similar to those of young versus aging animals. The results confirm the following: OS was significantly reduced (n=6-18/group) by exposure to EE versus NE exosomes, an effect that was abrogated by exposure of EE-exosomes to UV light.

| | |
|---|---|
| Control | 1.00 ± 0.071 |
| EE | 0.55 ± 0.03 *** |
| NE | 0.95 ± 0.08 |
| EE + UV | 0.99 ± 0.05. |

General Methods.

Experiments are performed in Wistar rats and hippocampal slice cultures. Slice cultures are prepared and used as previously described, using lysolecithin exposure as a means to evoke demyelination, and menadione to induce OS (Grinberg, et al., 2012; Eldh, et al., 2010). A newly developed rat enrichment cage (Lin, et al., 2008) is used for EE. Non-enriched (NE) control rats are individually housed in standard cages. A visual recognition task is used to assess changes in hippocampus-based memory (Obiang, et al., 2011)). The inventors screen for mRNAs using SABioscience PCR arrays and miRNAs using SeraMir exosome miRNA amplification kits followed by miRNA PCR arrays as previously described (Mitchell, et al., 2010). OS is measured using CellROX™ in slice cultures and OxyBlot™ kits (to determine carbonyl levels) in whole animals. MBP [measured via Western blot (slice) or immunostaining (hippocampus of whole animals)] are used as a measure of myelin content.

Briefly, the inventors assess the ability of exosomes from young animals to reduce demyelination and OS (from lysolecithin) in slice cultures, and OS, myelin, and cognitive loss from aging in animals. Results are compared to those from exosomes of aging animal blood.

The stimulation paradigm prior to exosome harvest is EE versus NE. Groups are: EE-young, NE-young, EE-aging and NE-aging. Exosomes from these animals are applied to slice cultures (A) or injected daily for seven days into naïve young and aging animals (B). Sham controls (for B) were injected daily with vehicle. mRNA and miRNA screening and subsequent confirmation of target proteins in brain are performed utilizing exosomes from groups defined above. Finally the inventors administer dendritic cell-derived exosomes engineered to contain specific RNA species (determined based on methods described above) to aging animals. Treatments are given intravenously or via nasal administration (Zhuang, et al., 2011) daily for seven days. Endpoints are as described above and are to determine the impact of exosome treatment on OS, myelin, and cognition (i.e., hippocampus-based memory) in whole animals and OS and myelin content in slice cultures.

Example 5: Exosome-Mediated Treatment

Dendritic cells can be used as a source for exosomes for mitigation of OS and increased myelination/remyelination. Exosomes may also be used to treat traumatic brain injury and neonatal brain injury.

General Methods.

Slice cultures are prepared and maintained as previously described (Grinberg, et al., 2012; Mitchell, et al., 2011; Pusic, et al., 2011). Oxidative stress is induced by brief exposure to the mitochondrial inhibitor, menadione (Grinberg, et al., 2012) and OS quantitated using CellROX™ imaging (Grinberg, et al., 2012). Exosomes are isolated using ExoQuick-TC™ isolation kits.

Dendritic cells are isolated from femurs and tibiae of $CO_2$-anesthetized and decapitated male rats (Wistar rats; 6-8 weeks old). After removing surrounding tissue, intact bones are disinfected with 70% ethanol for 2 min and rinsed with PBS before removing both ends. Then, a sterile syringe with a 21 gauge needle is used to flush marrow out with 10 mL of RPMI media through a cell strainer. Cells are then pelleted, treated with red blood cell lysis buffer, washed, and plated in culture media containing granulocyte-macrophage colony-stimulating factor at a density of 1 million cells/mL. After a week in culture, immature dendritic cells are collected. Finally, exosomes are harvested from media of cells treated with IFN-γ (Eldh, et al., 2010). Exosomes from IFN-γ-stimulated dendritic cells (IFN-γ-DC-Exos) are non-toxic (FIGS. 20A-20D).

Figures 21A, 21B, 21C:
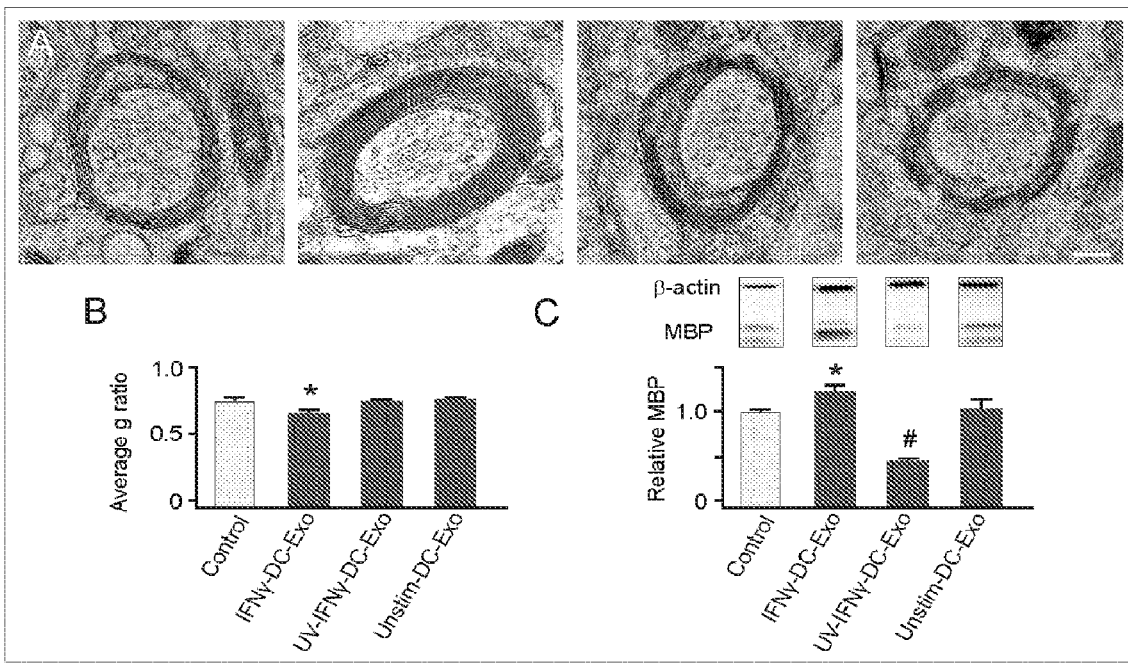
FIGS. 21A-21C. IFNγ-stimulated-DC-Exos increased myelination in slice cultures. (A) Exemplary electron microscopy images illustrate increased compact myelin in IFNγ-DC-Exo treated slice cultures. Treatments from left to right: control (no treatment); IFNγ-DC-Exo; UV-IFNγ-DC-Exo; and unstim-DC-Exo. Scale bar=200 nm. (B) Quantification of myelin g ratios from electron microscopy images (n=3 slices/group; and 10 cells/slice) showed a significant (*, p=0.008) increase in compact myelin thickness with IFNγ-DC-Exo treatment. (C) Western blot confirmation and quantification showed significant (*, p=0.02) increase in myelin basic protein levels in slice cultures treated with IFNγ-DC-Exo and a significant (#, p=<0.001; n=9, 15, 11, 9 slices/group, respectively) decrease in slice cultures treated with UV-IFNγ-DC-Exo. Significance was determined by ANOVA plus post hoc Holm-Sidak testing and ANOVA testing, respectively.

IFNγ-DC-Exos increase compact myelin levels in slice cultures. Different exosome treatments were applied to hippocampal slice cultures and EM imaging was performed three days later to determine changes in compact myelin. EM images demonstrated intact and tightly laminated myelin whose thickness was increased with the application of IFNγ-DC-Exos (FIG. 21A). Subsequent calculations of g ratios revealed significant (p=0.008) improvement of laminated myelin with IFNγ-DC-Exo treatment compared to control (FIG. 21B).

When applied to naïve 24 DIV hippocampal slice cultures, IFNγ-DC-Exos significantly (p=0.02) increased production of myelin basic protein (MBP) as measured via immunoblot (FIG. 21C). UV-treatment of IFNγ-DC-Exos (545 nm, 45 minutes 100 µWatts/cm$^2$) prior to application abrogated this effect, indicating involvement of RNA species in the observed increase in myelin production (Eldh et al., 2010). Additionally, a significant (p<0.001) decrease of MBP levels was seen with UV-treatment of IFNγ-DC-Exos compared to control (FIG. 21C). This is likely due to the delivery of contents damaged through UV treatment.

Figures 22A, 22B, 22C, 22D:
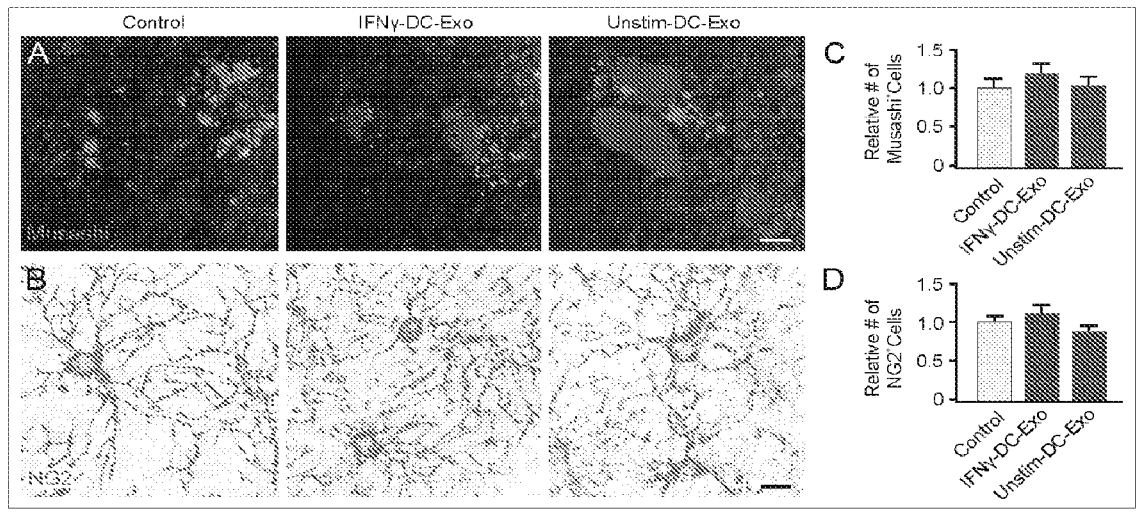
FIGS. 22A-22D. Progenitor cell populations were not affected by IFNγ-stimulated-DC-Exo treatments. Confocal typical images are shown for (A) neural stem cells (musashi, top) (B) oligodendrocyte progenitor cells (NG2, bottom) in control untreated slice cultures (left panel), IFNγ-stimulated-DC-Exos treated slice cultures (middle panel), and unstimulated-DC-Exos treated slice cultures (right panel). Scale bar=10 µm. Quantification of the number of positive (C) neural stem cells and (D) oligodendrocyte progenitor cells in each treatment group (determined from 9 images/group and n=3/group). No significant differences were seen between groups via ANOVA plus post hoc Holm-Sidak testing.

IFNγ-DC-Exo treatment does not cause progenitor depletion. To determine whether exosome-mediated increase of OPC differentiation has a deleterious effect on progenitor populations, the presence of neural progenitor cells and OPCs were assessed in hippocampal slice cultures treated with IFNγ-DC-Exos and Unstimulated-DC-Exos compared to untreated control. Staining with Musashi (Msi1/Msi2) (FIG. 22A) for neural stem cells revealed no significant difference in the number of positive cell counts between exosome treated slices and control (FIG. 22B). Similarly, staining with NG2 for cells in the oligodendrocyte progenitor cell stage showed no significant difference in the number of positive cells (FIGS. 22C-D), suggesting that the progenitor pool was not affected.

Figures 4A, 4B:
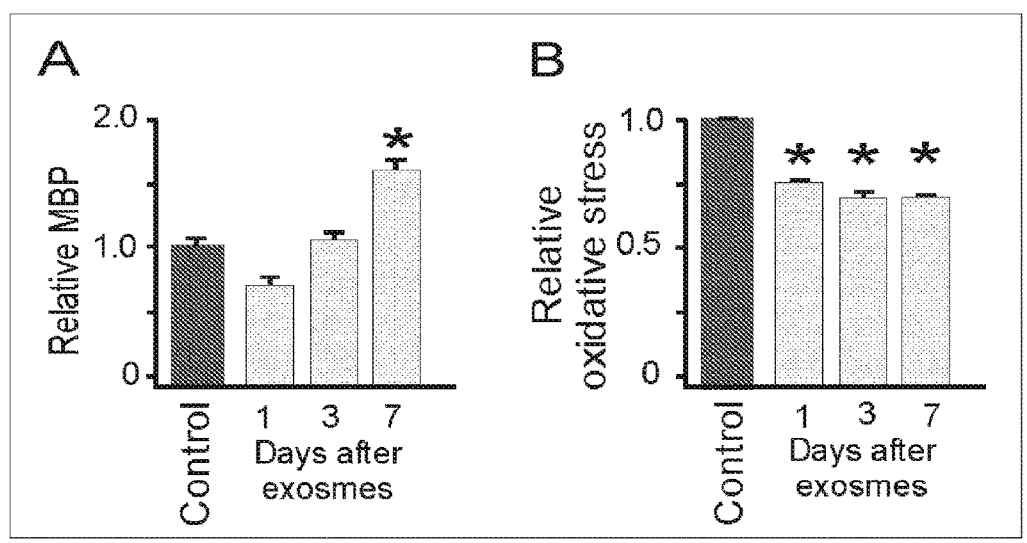
FIGS. 4A-4B. Physiological and transient (i.e., phasic, to emulate conditions of environmental enrichment (EE) consisting of exercise-rest-exercise cycles) stimulation with IFN-$\gamma$ triggered nutritive effects. Transient (i.e., 500 U/mL× 12 hours; all groups n≥5) exposure of hippocampal slice cultures was nutritive when assessed seven days later. (A) myelin basic protein (MBP) was significantly ($p\leq0.001$) increased above baseline and (B) OS was significantly ($p\leq0.001$) reduced. OS was induced by via exposure to mitochondrial inhibition (via menadione).
Figures 5A, 5B:
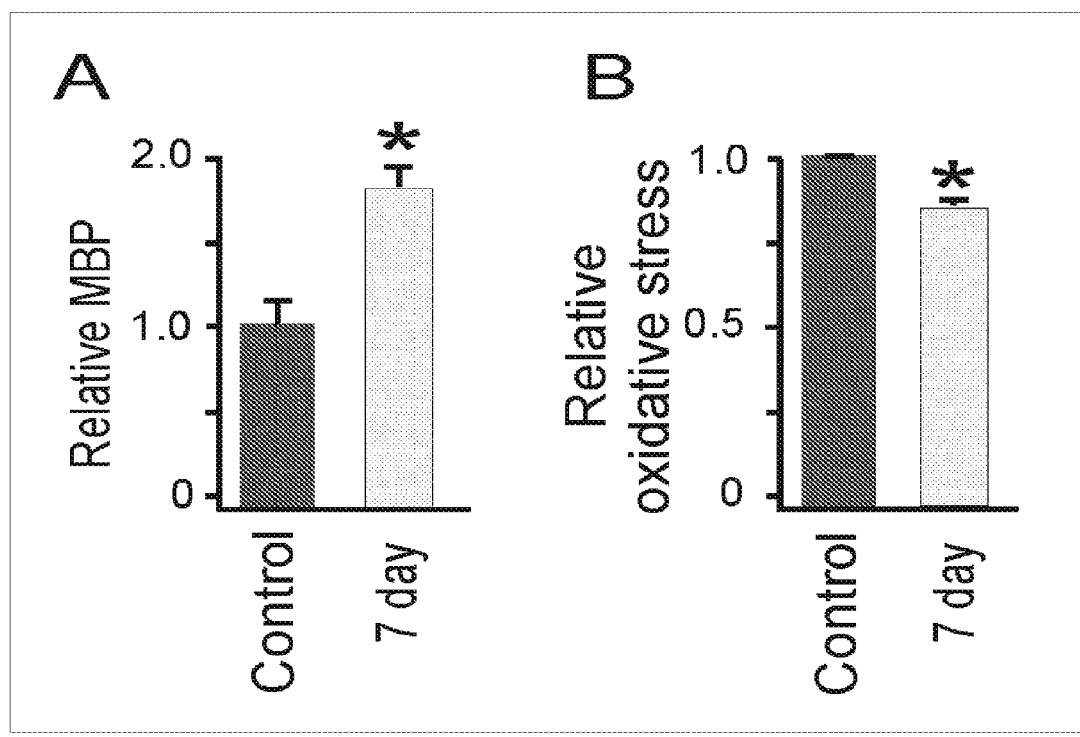
FIGS. 5A-5B. IFN-$\gamma$, when pulsed onto slice cultures for 12 hours triggered the release of nutritive exosomes that mimic the nutritive effect of pulsed exposure to IFN-$\gamma$. Hippocampal slice cultures were exposed to IFN-$\gamma$ (500 U/mL×12 hours) and three days later exosomes were harvested from their surrounding incubation media. The latter were then applied to naïve slice cultures and measurements made seven days later. All group sizes were ≥5; all significance measurements $p\leq0.001$. (A) Exosomes from IFN-$\gamma$ stimulated slice cultures triggered a significant rise in MBP above baseline levels and (B) a significant reduction in OS. OS was induced by via exposure to mitochondrial inhibition (via menadione).
Figures 6A, 6B:
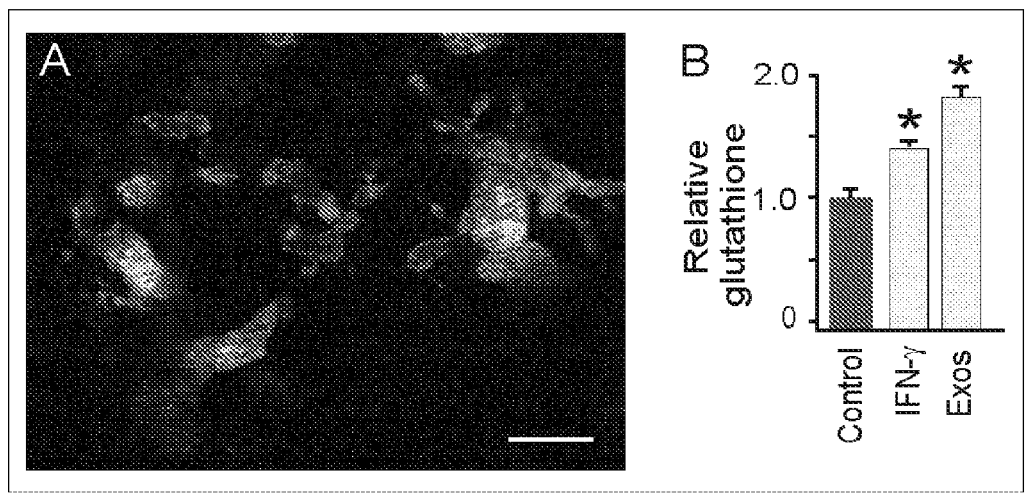
FIGS. 6A-6B. In addition, pulsed IFN-$\gamma$ or exosomes significantly increased the anti-oxidant glutathione in microglia within hippocampal slice cultures, consistent with the increased resistance to OS seen in peripheral mast cells (Eldh M, et al. (2010). PLoS ONE 5(12): e15353). The inventors detected an IFN-$\gamma$-induced rise in slice culture glutathione using ThiolTracker™, a fluorescent indicator of glutathione. (A) Confocal imaging for glutathione (long arrow) and a microglia marker (short arrow) confirmed that pulsed exposure to IFN-$\gamma$ selectively increases microglial glutathione. Scale bar=10 µm. (B) Furthermore, this increase was significant ($p\leq0.001$; n≥5/group) and could be mimicked by exposure to exosomes isolated from slice cultures activated by pulsed-exposure to IFN-$\gamma$.
Figure 7A:
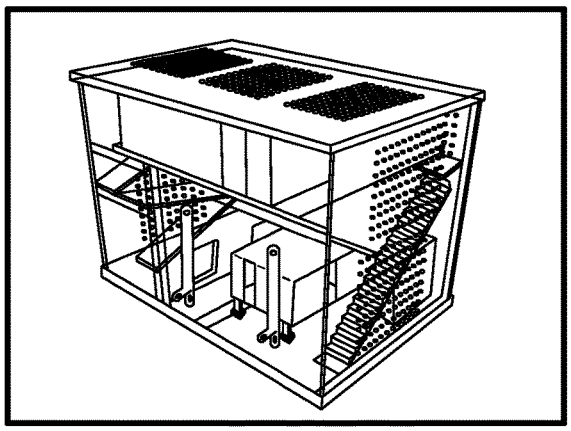
FIGS. 7A-7F. Marlau-style enrichment cage (Obiang, et al., 2011; Sanchez, et al., 2009) is shown where rats have free access to food and water, a maze, running wheel, and socialization area for 4 weeks to provide increased volitional opportunities for intellectual, physical, and social stimulation (i.e., EE). Non-enriched rats (NE) rats are housed in single standard cages. The EE cage consists (A) of a large two layer environment where a top layer maze (B) is changed three times a week (i.e., Monday, Wednesday, and Friday). Complexity is provided by the maze and novelty by changing the maze frequently as noted. (C) Activity is provided by a running wheel and (D) socialization by a red plastic resting area. (E) Rats climb a ladder to progress through the maze and (F) descend ramps to enter a feeding area. They move from the feeding area to the large socialization/exercise area via one-way doors.
Figure 7B:
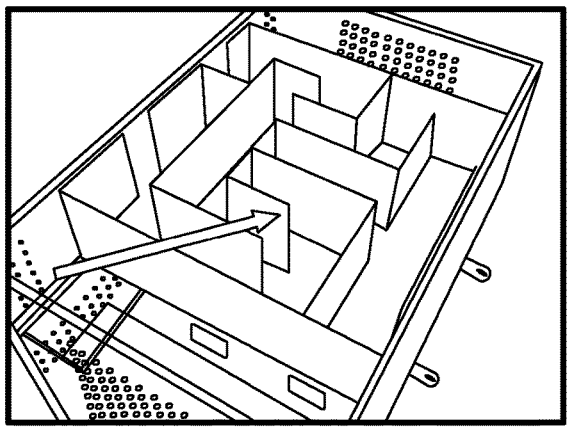
Figure 7C:
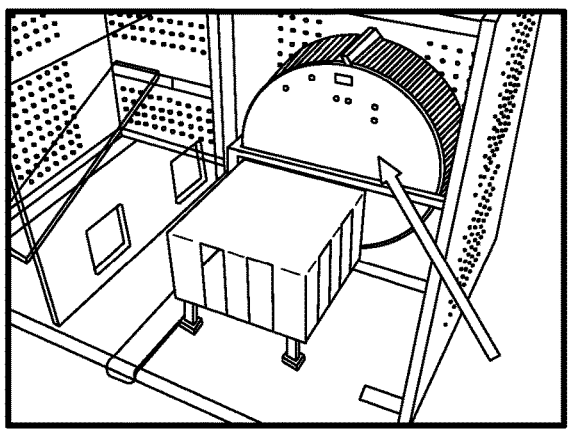
Figure 7D:
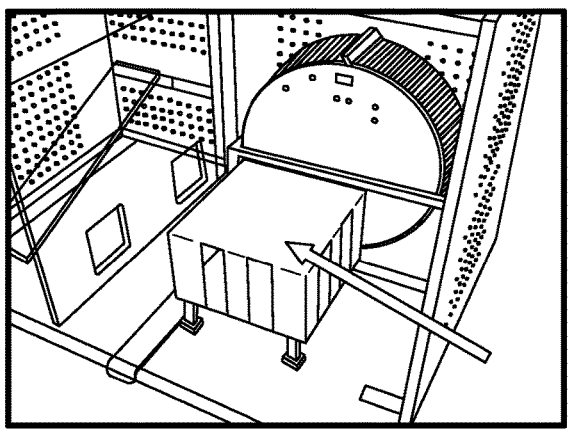
Figure 7E:
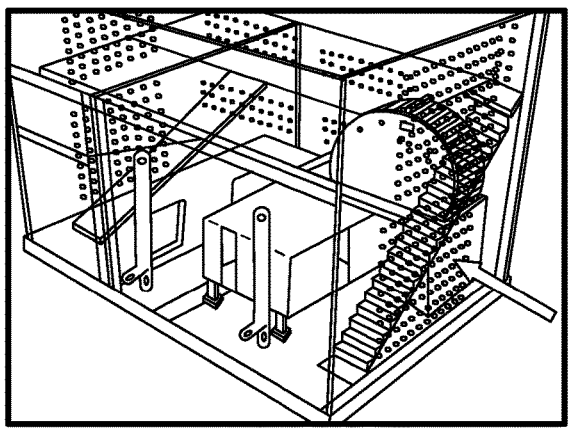
Figure 7F:
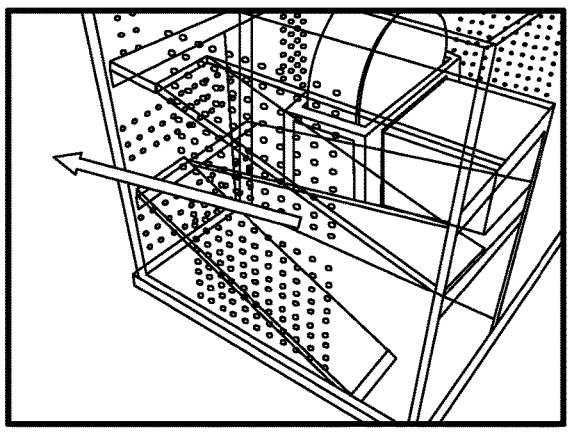
Figures 23A, 23B, 23C, 23D:
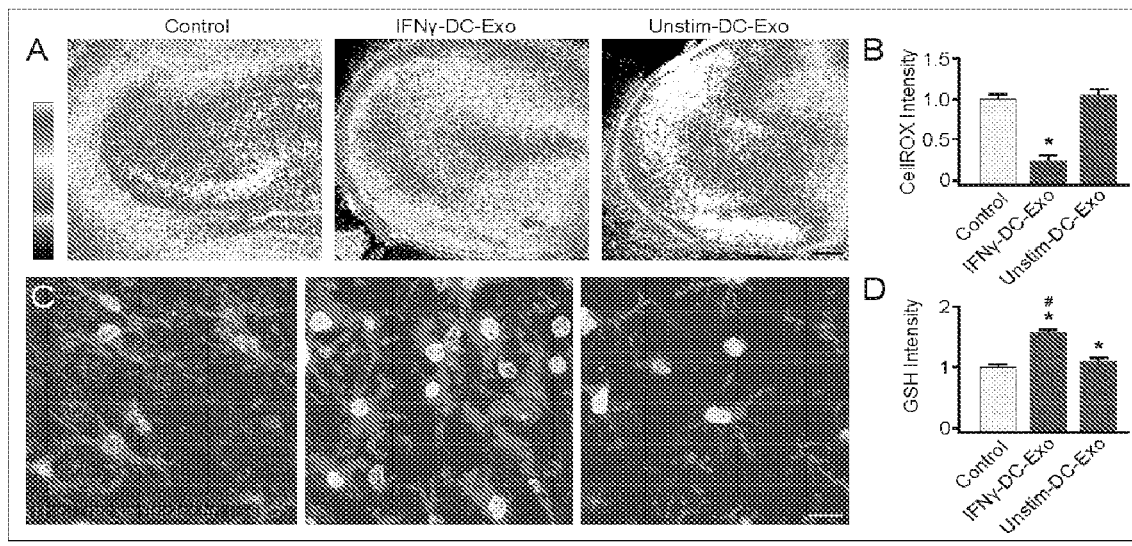
FIGS. 23A-23D. IFNγ-stimulated-DC-Exos reduced oxidative stress in slice culture. (A) Exemplary images show oxidative stress induced by acute exposure to menadione measured via CellROX™, a fluorescent marker of oxidative stress after exposure to menadione alone (left) and after treatment with IFNγ-stimulated-DC-Exos (middle) and unstimulated-DC-Exos (right). Scale bar=200 µm. Quantification of fluorescence intensity (B) was performed at the CA3 area and showed that IFNγ-stimulated-DC-Exo treatment significantly (*, p<0.001; n=8/group) reduced oxidative stress. (C) Exemplary images show glutathione (ThiolTracker™) and microglia (IsolectinB4) costaining. Control (left), IFNγ-stimulated-DC-Exos (middle) and unstimulated-DC-Exos (right). Scale bar=10 µm. (D) Quantification of ThiolTracker™ fluorescence intensity revealed a significant (*, p<0.001; n=9) increase in glutathione content of microglia after treatment with IFNγ-stimulated-DC-Exos and unstimulated-DC-Exos compared to control. Significance was determined by ANOVA plus post hoc Holm-Sidak testing.

IFNγ-DC-Exo treatment also significantly increased oxidative tolerance of slice cultures. Administration of these exosomes three hours prior to menadione exposure significantly (p<0.001) reduced oxidative stress, as seen by CellROX™ staining (FIGS. 23A-23B). Reduced glutathione levels, measured via ThiolTracker™ staining, were significantly (p=<0.001) increased in cultures treated with both exosomes compared to untreated controls (FIGS. 23C-23D). However, treatment with IFNγ-DC-Exos triggered a significantly greater rise in reduced glutathione than that seen with unstimulated-DC-Exos alone. Glutathione was found localized to microglia, as seen by isolectin-GS-IB$_4$ double staining (FIG. 4C).

Figure 26:
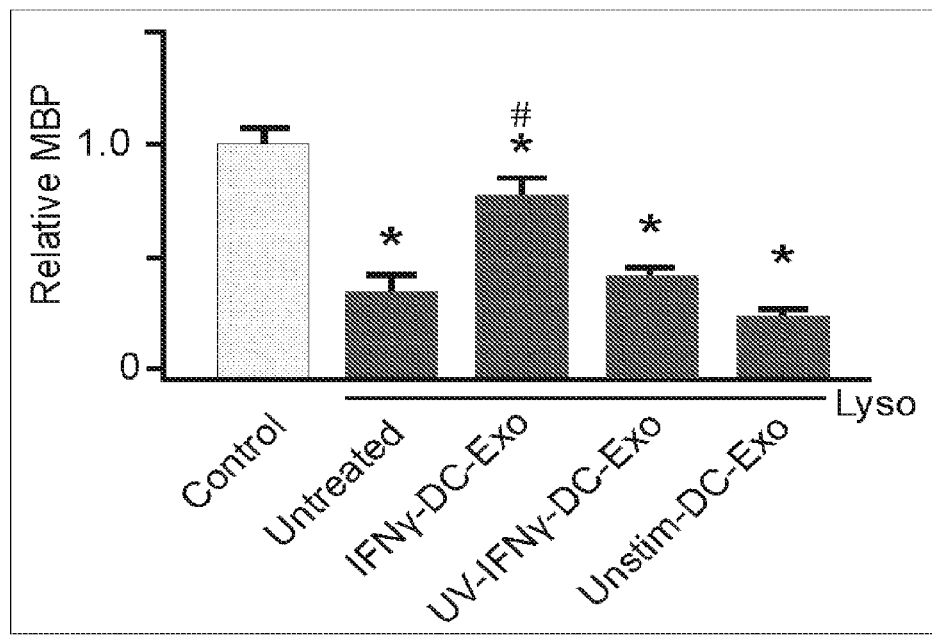
FIG. 26. IFNγ-stimulated-DC-Exos increased remyelination after acute lysolecithin induced demyelination. Slice cultures were exposed to lysolecithin to model acute demyelination followed by remyelination, then given different exosome treatments. At five days post-treatment, at the onset of remyelination, cultures were harvested and MBP content quantified via Western blot. While lysolecithin (Lyso) exposure caused a significant (*, p<0.001; n=9 slices/group) reduction of MBP in all groups compared to control, treatment with IFNγ-stimulated-DC-Exo induced a significant (#, p<0.001) increase in remyelination compared to all other lysolecithin exposed groups. Significance was determined by ANOVA plus post hoc Holm-Sidak testing and ANOVA testing, respectively.

Additionally, IFNγ-DC-Exos restore myelin levels post lysolecithin-induced demyelination. Lysolecithin was used as a means to induce demyelination, as a model of MS in hippocampal slice cultures (Birgbauer, et al., 2004). Treatment with IFNγ-DC-Exos post lysolecithin exposure significantly (p<0.001) increased recovery of myelin, measured at five days post injury, compared to cultures treated with lysolecithin alone or given UV-IFNγ-DC-Exos (FIG. 26).

Figures 24A, 24B:
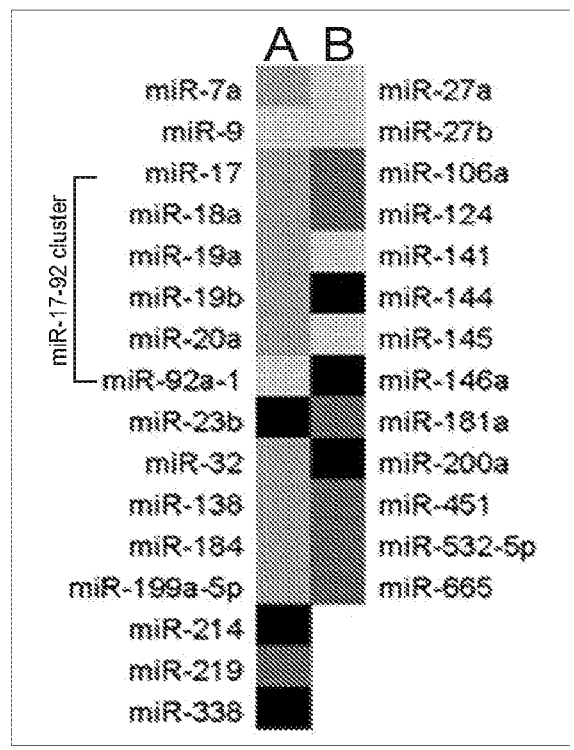
FIGS. 24A-24B. IFNγ-stimulated-DC-Exo were enriched in miRNA species involved in myelin production and anti-inflammatory response. miRNA content of IFNγ-stimulated stimulated-DC-Exos were compared to that of unstimulated-DC-Exos. Results show expression levels of specific miRNAs involved in (A) myelin production/oligodendrocyte differentiation and (B) anti-inflammatory response. Black panels indicate mature miRNA species that could not be detected; medium light grey panels indicate miRNAs that were readily detectible but not significantly enriched; light grey indicate significantly enriched (i.e., >2 fold) miRNAs; and dark grey indicates very highly enriched (i.e., >10 fold) miRNAs.

Specific miRNAs involved in oligodendrocyte differentiation and anti-inflammatory pathways are highly enriched in IFNγ-DC-Exos. Screening of exosomal miRNA revealed significant differences between the contents of IFNγ-DC-Exos and unstimulated-DC-Exos. IFNγ treatment of DC cells increased expression and packaging into exosomes of miRNAs involved in oligodendrocyte differentiation and myelin production pathways, listed in FIG. 24A. Notably, miR-219 was highly enriched in IFNγ-DC-Exos and undetectable in Unstimulated-DC-Exos. miRNA species involved in regulation of inflammatory pathways, such as miR-181a, miR-451, miR-532-5p, and miR-665 were especially highly enriched (>10 fold) in IFNγ-DC-Exos versus unstimulated-DC-Exos shown in FIG. 24B. Increased presence of these miRNA species indicates the possibility that IFNγ-DC-Exos may reduce inflammation and oxidative stress.

Figures 25A, 25B, 25C, 25D:
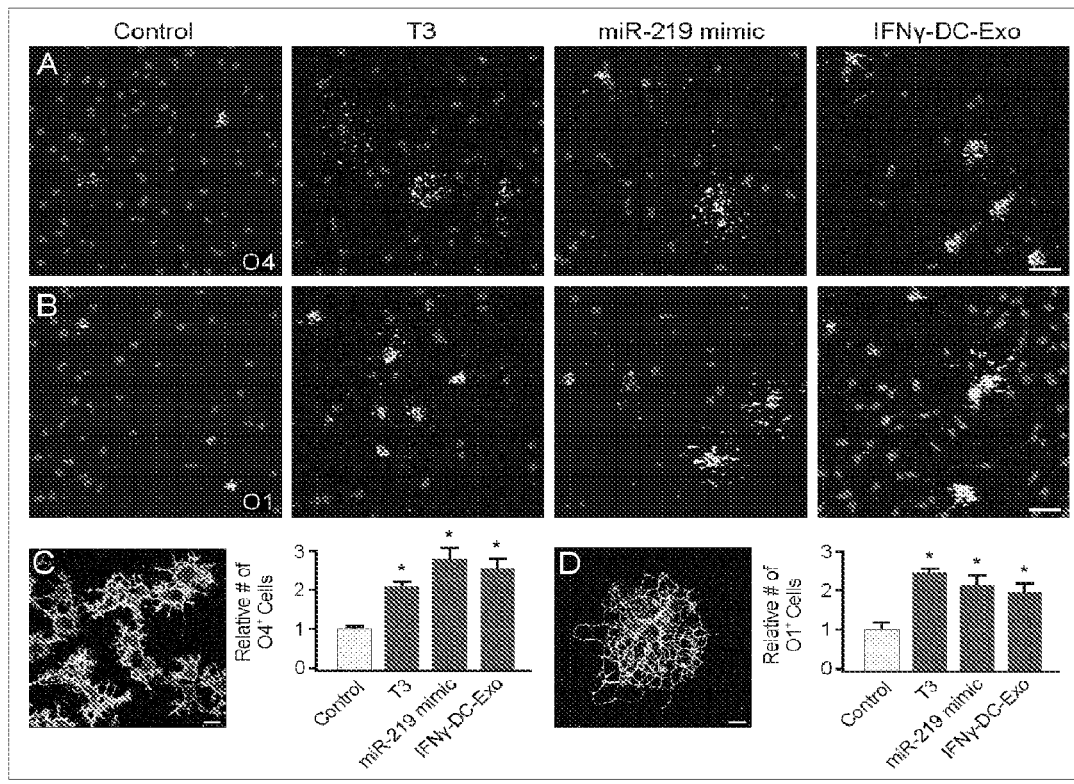
FIGS. 25A-25D. miR-219 mimic and IFNγ-stimulated-DC-Exos similarly promote OPC differentiation. (A) Representative images of O4 positive staining with DAPI counterstain. (B) Representative images of O1 positive staining with DAPI counterstain. Scale bar=20 µm. (C) Exemplary high-powered image of O4 staining to illustrate morphology, and quantification of percent of O4 positive cells (O4$^+$ cells/total DAPI$^+$ cells) per field (3 images per coverslip, n=3 coverslips/group). Treatment with miR-219 mimic and IFNγ-stimulated-DC-Exos stimulated differentiation of OPCs into O4 expressing cells similar to T3 supplementation, and all groups were significantly (*, p<0.001) increased from control. (D) Exemplary high-powered image of O1 staining to illustrate morphology, and quantification of percent of O1 positive cells (O1$^+$ cells/total DAPI$^+$ cells) per field (3 images per coverslip, n=3 coverslips/group). Treatment with miR-219 mimic and IFNγ-stimulated-DC-Exos stimulated differentiation of OPCs into mature O1 expressing cells similar to T3 supplementation, and all groups were significantly (*, p=0.002) increased from control. Significance was determined by ANOVA plus post hoc Holm-Sidak testing.

To determine if IFNγ-DC-Exos increase OPC differentiation through miR-219, a miR-219 mimic was applied to primary OPC cultures. Primary OPC cultures were grown at low density on glass coverslips, and either treated with IFNγ-DC-Exos or transfected with a miR-219 mimic. Supplementation with T3, which induces OPC differentiation, was used as a positive control. Three days after treatment, IFNγ-DC-Exo treated OPCs showed increased differentiation compared to control cultures, as determined by increased staining for O4 (FIG. 25A) and O1 (FIG. 25B) positive cells. OPC cultures transfected with the miR-219 mimic likewise showed increased differentiation (FIGS. 25A-25B). Quantification of the percent O4 and O1 positive cells per treatment group revealed that both IFNγ-DC-Exos and the miR-219 mimic promoted OPC differentiation to the same extent as treatment with T3 (positive control), and were significantly (p=0.002 and p<0.001, respectively) increased from control (FIGS. 25C-25D).

Figures 27A, 27B:
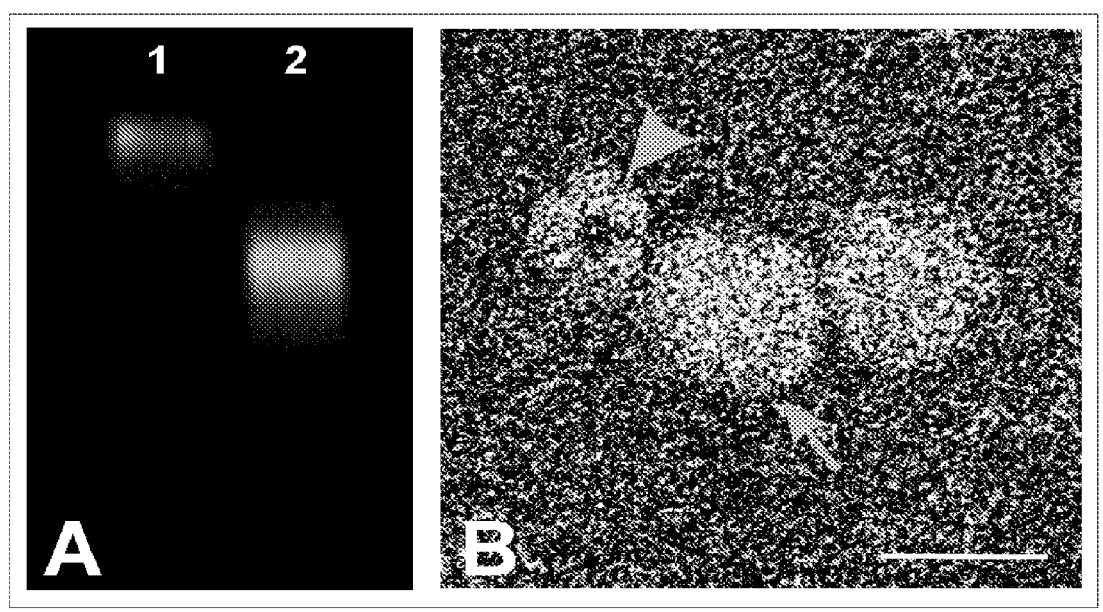
FIGS. 27A-27B. Confirmation of exosome quantum dot (QD) tagging. (A) Agarose gel electrophoresis of unconjugated QD nanoparticles (Lane 1) and CD63-conjugated QD nanoparticles (Lane 2). (B) Electron microscopy image of QD nanoparticle (arrowhead) tagged to exosomes (arrow). Scale bar=25 nm.

Quantum dot (QD) tagged IFNγ-DC-Exos are preferentially taken up by oligodendroctyes. To determine whether QD nanoparticles was successfully conjugated to anti-CD63 antibody, unconjugated QD nanoparticles and conjugated QD-CD63 were analyzed on a 1.5% agarose gel. Conjugated QD-CD63 (FIG. 27A, lane 2) migrated at a higher molecular weight in comparison to unconjugated QD (FIG. 27A, lane 1) indicating the successful conjugation and a homologous species of conjugated QD-CD63. Further confirmation of the coupling of QD-CD63, seen as a circular structure with an electron dense core (FIG. 27B, arrowhead), to exosomes (FIG. 27B, arrow) was visualized by EM imaging.

QD-IFNγ-DC-Exos (FIG. 28A) and QD-unstimulated-DC-Exos (FIG. 28B) were applied to hippocampal slice cultures and immunostained for specific cell types. Tracking of both types of QD-Exos resulted in co-localization with oligodendroctyes, microglia, and astrocytes at different rates; no uptake in neurons was observed.

Figures 28A, 28B, 28C:
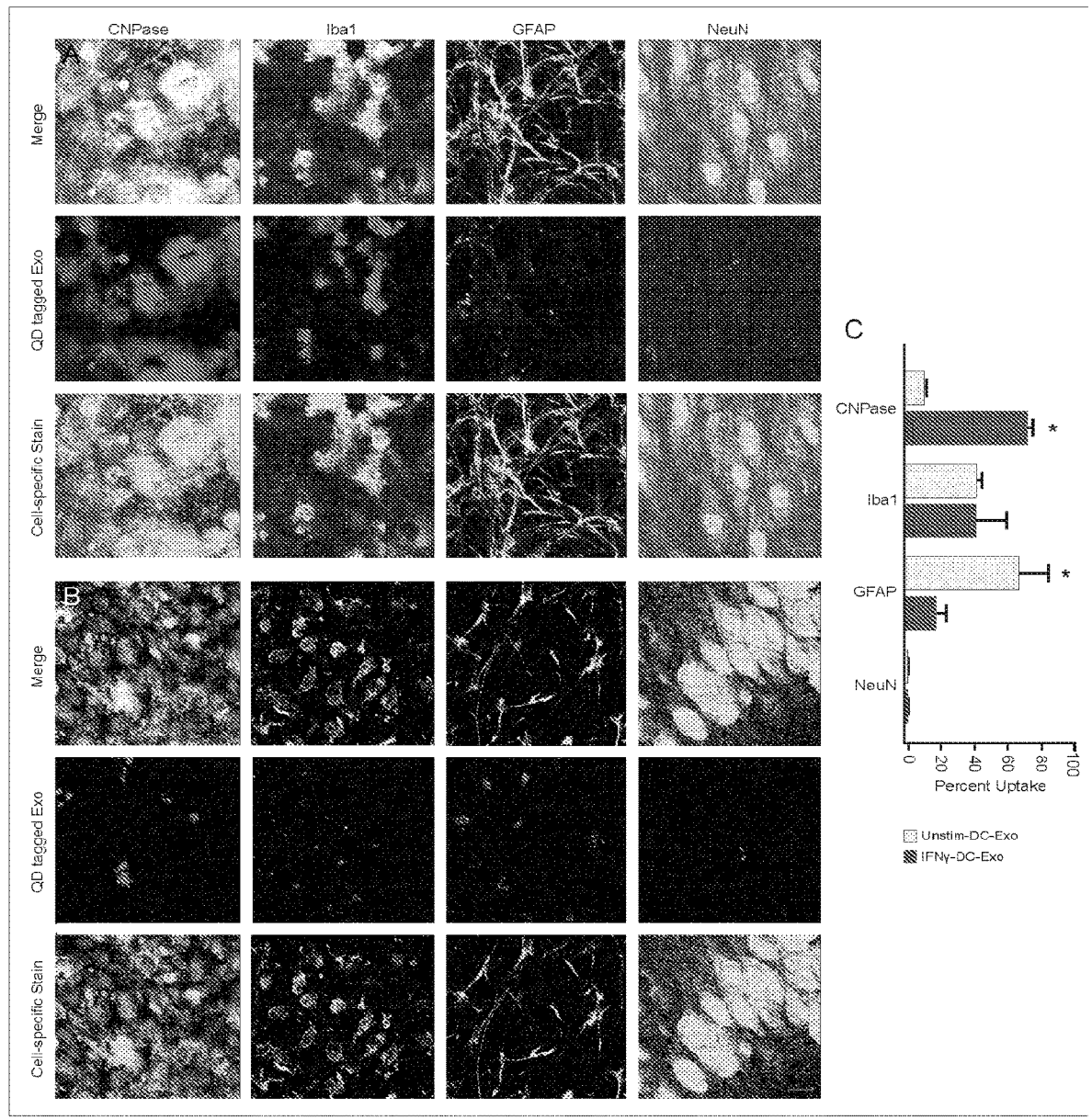
FIGS. 28A-28C. IFNγ-stimulated-DC-Exos preferentially enter oligodentrocytes. (A) Merged images (top row) of QD tagged IFNγ-stimulated-DC-Exos (middle row) and cell-specific immunofluorescence (bottom row). (B) Merged images (top row) of QD tagged unstimulated-DC-Exos (middle row) and cell-specific immunofluorescence (bottom row). Left to right: oligodendroctyes (anti-CNPase), microglia (anti-Iba1), astrocytes (anti-GFAP), and neurons (anti-NeuN). Scale bar=10 µm. (C) Percent uptake of QD tagged IFNγ-stimulated-DC-Exos and QD tagged unstimulated-DC-Exos for each cell type. Percent uptake calculated per 60 cells from n=3 slices/group. These results indicate that DC exosomes can track to specific brain cell types. IFNγ-stimulated-DC-Exos were significantly (*, p<0.001) localized to oligodendrocytes, while unstimulated-DC-Exos were significantly (*, p<0.001) localized to astrocytes. Significance was determined by Student's t-test.

QD positive cells are listed as a percentage of cells measured (FIG. 28C). The inventors counted 60 cells per cell-specific staining group and noted the number of QD-positive cells. QD-IFNγ-DC-Exos in slice showed that they were preferentially taken up by oligodendroctyes (72%) and to a lesser extent microglia (34%) and astrocytes (12%). In comparison, QD-unstimulated-DC-Exos were found to also co-localize with oligodendroctyes but to a lesser extent (7%), with uptake by microglia being similar (38%) to QD-IFNγ-DC-Exos, and astrocytes having the highest uptake at 63%. This suggests a difference in surface composition, where IFNγ-DC-Exos are significantly (p<0.001) targeted to oligodendroctyes and unstimulated-DC-Exos are significantly (p<0.001) targeted to astrocytes.

Figures 16A, 16B, 16C:
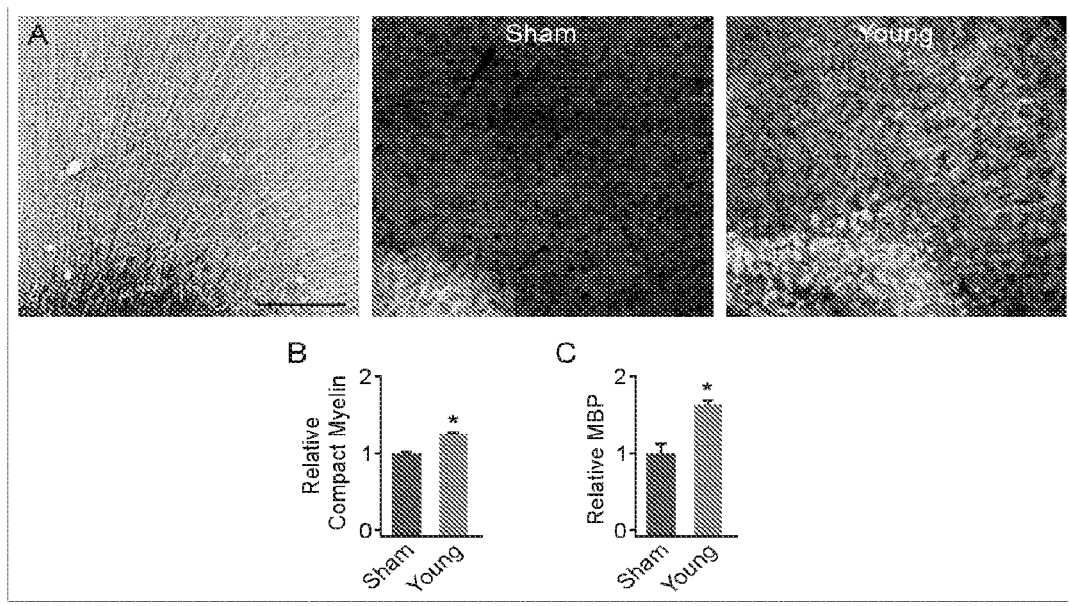
FIGS. 16A-16C. Nasal administration of young serum-derived exosomes increased myelin in aging rats. 50 µL of exosomes (~100 µg protein) were intranasally delivered to aging rats. Three days later, brains were harvested, frozen, and motor cortex sectioned (14 µm) for staining (A) Staining for myelin basic protein (MBP) demonstrates myelin distribution in parasagittal motor cortex (left). Exemplary images illustrate corresponding cytochemical staining with Fluoro-Myelin™ to measure levels of compact myelin after nasal administration of UV-exposed sham exosomes (center) or young serum-derived exosomes (right). Stronger staining intensity at bottom of all images delineates the underlying white matter. Scale bar=250 µm. (B) Quantification of staining intensity shows significantly (*p=0.001; n=3 animals/group, with 9 images quantified per animal) increased compact myelin in cortex of animals treated with young exosomes. (C) Western blot for MBP confirms staining results and shows significantly (*p=0.01; n=3 animals/group) increased MBP in cortex of animals treated with young exosomes. Significance was determined by ANOVA plus post hoc Holm-Sidak testing.
Figures 17A, 17B, 17C, 17D:
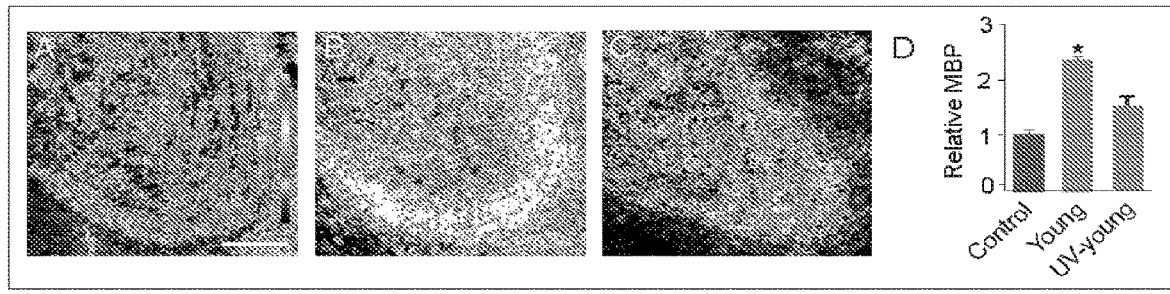
FIGS. 17A-17D. Myelin increased from nasal application of exosomes. Rats were anesthetized with isoflurane and 50 µL of exosomes (~100 µg protein) delivered nasally. Three days later, brains were harvested. Images show olfactory bulb FluoroMyelin™ fluorescence in control (A) exosome treated (B) or UV-exposed exosome treated (C) cultures. (D) Quantification shows the EE-exosomes triggered a significant increase (*p<0.001) in olfactory bulb compact myelin that was abrogated to with administration of UV exposed EE-exosomes (UV-Exo). Significance was determined by ANOVA plus post hoc Holm-Sidak testing.
Figures 18A, 18B, 18C, 18D:
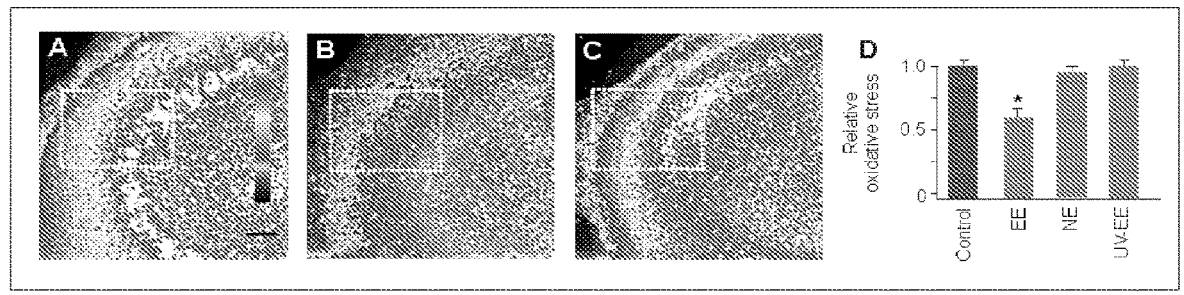
FIGS. 18A-18D. EE-exosome-induced reduction in oxidative stress. OS was induced by menadione and measured via a fixable fluorescent marker for reactive oxygen species.[35] Representative images are shown under control (A) conditions and three days after exposure to EE-exosomes (B) and NE-exosomes (C). Scale bar=200 µm. (D) Quantifications show EE-exosome application for three days triggered a significant (*p<0.001) reduction in OS, compared to control, NE-exosomes, and UV exposed EE-exosomes. Significance was determined by ANOVA plus post hoc Holm-Sidak testing.

Exosomes can be used to treat whole animals. Nasal administration of young serum-derived exosomes increased myelin in aging rats. 50 μL of exosomes (~100 μg protein) were intranasally delivered to aging rats. Three days later, brains were harvested, frozen, and motor cortex sectioned (14 μm) for staining. Cortices of animals treated with young exosomes had significantly increased compact myelin (FIGS. 16A-16C). Similar increases in myelin were observed in olfactory bulbs (FIGS. 17A-17D).

Figures 19A, 19B, 19C:
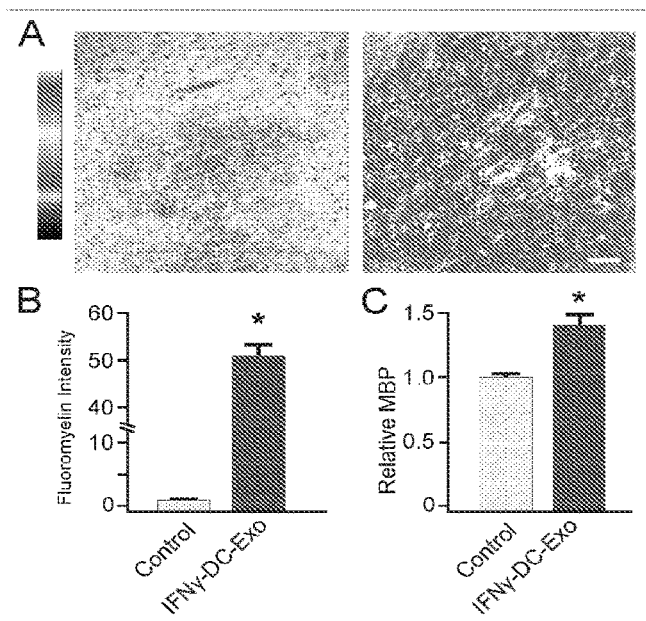
FIGS. 19A-19C. Nasal administration of IFNγ-stimulated-DC-Exos increased production of myelin in cortex. (A) Three days after nasally administered PBS-sham (left) or IFNγ-stimulated-DC-Exos (right), brains were harvested, frozen, and cortex sectioned for staining with FluoroMyelin™ to measure levels of compact myelin. Cal bar, 100 µm. (B) Quantification showed a significant (*, p<0.001; n=3 animals/group) increase in FluoroMyelin™ staining intensity following nasal administration of IFNγ-stimulated-DC-Exos. (C) Western Blot for MBP shows a significant (*, p=0.019; n=3 animals/group) increase in MBP levels in the parasagittal motor cortex area of animals treated with IFNγ-stimulated-DC-Exos. Motor cortex was chosen as an exemplary area of brain. Significance was determined by Student's t-test.
Figures 20A, 20B, 20C, 20D:
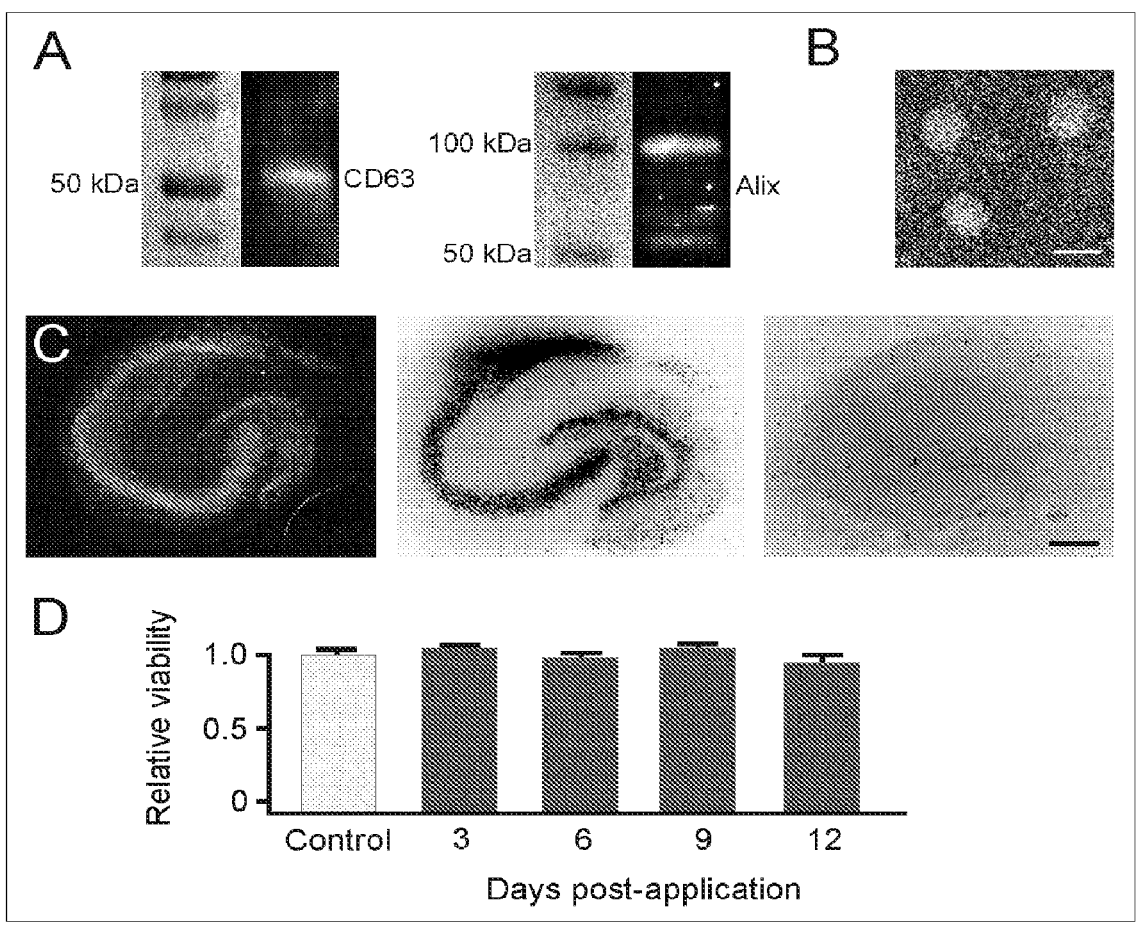
FIGS. 20A-20D. IFNγ-stimulated dendritic cells produced non-toxic exosomes. Exosome isolation confirmed by (A) Western Blot for surface markers CD63 and Alix, and by (B) electron microscopy. Scale bar=25 nm. (C) Exosome application to slice cultures showed no toxic effects. Slices were stained with Sytox at 3, 6, 9, and 12 days post-treatment. NeuN immunostaining image (left) shows normal neuronal architecture. Sytox positive image (center) shows a control with neuronal injury induced by 24 hour exposure to 20 µM N-methyl-d-aspartate. Sytox negative image (right) of exosome treated culture showed no injury. Images were inverted to enhance visualization. Scale bar=250 µm. (D) Quantification of Sytox fluorescence intensity (n=9 slices/group) confirmed no significant change (ANOVA plus post hoc Holm-Sidak testing).

Similarly, nasal administration of exosomes from IFNγ-stimulated dendritic cells (IFNγ-DC-Exos) increases production of cortical myelin (FIGS. 19A-19C). To assess the ability of IFNγ-DC-Exos to increase myelin in vivo, IFNγ-DC-Exos were nasally administered to rats and their ability to increase myelin in vivo was determined. Three days post-nasal administration, brains were harvested and increased myelination was observed in the motor cortex by FluoroMyelin™ staining (FIG. 19A). FluoroMyelin™ staining intensity was significantly (p<0.001) higher in IFNγ-DC-Exos treated animals than sodium succinate treated (sham) animals (FIG. 19B). Western blot analysis similarly showed significantly (p=0.019) increased MBP levels in the cortex of animals treated with IFNγ-DC-Exos compared to sham (FIG. 19C).

Further effects of exosome treatment may be demonstrated with testing of hippocampus-based memory. The visual recognition task is used to assess changes in hippocampus-based memory. This task is non-stressful and robustly tests hippocampus-dependent memory (Gobbo & O'Mara, 2004). Recognition of a novel object versus a familiar one is used as a measure of hippocampus-dependent memory. The visual recognition task consists of four phases: habituation, training, retention, and test. Rats with normal object recognition memory will show an increase in exploration of a novel object versus a familiar one. Memory testing is quantified as the amount of time spent exploring the novel object as a percentage of the total time spent exploring both objects during the first 5 min of the testing phase.

Rats are an optimal species for aging/cognition research (Gallagher, et al., 2011). The inventors used the Wistar strain because of its greater ambulatory behavior compared to other strains, which aids in EE-related aging research.

Exosome effects on OS after administration to whole animals may be determined via OxyBlot™ measurement of protein carbonyl levels. The inventors plan to deliver exosomes to briefly anesthetized rats daily for seven days before harvest and measurement of experimental variables. To determine if proteins contribute to exosome-induced reduction of OS, the inventors may (a) expose slice cultures to IFNγ for three days, harvest exosomes from media, and use an in vitro translation assay coupled to mass spec analysis (Valadi, et al., 2007). The inventors will also (b) select proteins/peptides of interest from the aforementioned screen, and add them to slice cultures to determine if they can mimic application of IFNγ/OS-stimulated neural exosomes to reduce OS and increase myelin (i.e., MBP and thicked myelin measured by electron microscopy).

Groups are: (a) control slices; (b) slices exposed to stimulated exosomes; (c) slices exposed to stimulated exosomes depleted of RNA via UV light exposure; and (d) slices exposed to unstimulated exosomes.

The inventors use UV light to inactivate exosomal RNA as a sham control. This procedure effectively removes cell transfer of OS resistance in immune cells (Eldh, et al., 2010), suggesting the effective OS protection from exosomes involves mRNA or miRNA, not protein.

Example 6: Exosome-Mediated Mitigation of Oxidative Stress and Demyelination

IFNγ has detrimental and beneficial brain effects, consistent with physiological conditioning hormesis (Kraig, et al., 2010). IFNγ worsens demyelination from EAE, a model of multiple sclerosis. Yet, low-level IFNγ before the onset of disease protects against demyelination, an effect involving an oligodendrocyte oxidative stress response (OSR; Lin, et al., 2008). Also, spreading depression (SD) triggers a transient (1 & 3 but not 7 day) drop in MBP in rat hippocampal slice cultures (Kunkler, et al., 2006); and demyelination increases SD susceptibility in vivo (Merkler, et al., 2009).

Since T cells are present in hippocampal slice cultues and SD increases their production of IFN-γ (Pusic, et al., 2010), the inventors examined how T cells and IFN-γ affect SD susceptibility (Pusic, et al., 2011). Results were based on n≥3-6/group and comparisons made v. shams.

PCR arrays showed a 3.61 fold increase in osteopontin and a 2.22 fold decrease in IL-10, which indicate an enhanced Th1 effect from SD. Exposure to the Th1 cytokine IFNγ (500 U/mL) triggered significantly increased susceptibility to SD at 1 day but, importantly, triggered a significantly reduced susceptibility at 3 days. Removal of IFNγ by depletion of T cells by anti-CD4 or a neutralizing anti-IFNγ antibody prevented altered susceptibility to SD and prevented the SD-induced demyelination which otherwise triggered ruptured myelin sheaths shown via EM. Neocortical SD in vivo triggered a similar reduction in MBP a day later.

Finally, three-day treatment with IFNγ (500 U/mL) significantly reduced reactive oxygen species generated from chemical long-term potentiation (cLTP), a physiological means to increase brain excitability like that seen hours after SD (Grinberg, et al., 2011). This beneficial effect of low-level IFNγ is supported by results from mice where enrichment, which occurs with hippocampal learning (Kraig, et al., 2010), triggered a significant elevation in hippocampal T-cells, IFN-γ and MBP.

These results show that SD acutely activates T cells and may overwhelm the brain's oxidative tolerance, resulting in increased susceptibility to SD and demyelination. These effects may be prevented via enrichment, which modulates immune parameters that favor a Th1-skewed response (i.e., low-level IFNγ production) extended over time. Our efforts are directed at deciphering neuroimmune signaling responsible for these dual effects of T cells and how they relate to an activity-dependent stress response as a means to develop novel therapeutics that prevent recurrent migraine and its transition to chronic migraine.

Example 7: Exosome-Mediated Mitigation of Spreading Depression (Migraine)

The detrimental effects of T cell-secreted interferon gamma (IFN-γ) on oxidative stress (OS) and demyelination in multiple sclerosis are well recognized. However, it is also known that before disease onset low levels of IFN-γ, like that produced by EE, protect against demyelination and reduce OS. SD elevates IFN-γ, and SD threshold (SDT) is decreased in experimental models of demyelination, suggesting involvement of T cells in SD. Since the inventors found T cells within rat hippocampal slice cultures, the inventors utilized this preparation to probe for T cell-mediated effects of IFN-γ on spreading depression threshold, OS, and MBP levels. SD triggered a significant loss of MBP that gradually recovered by seven days, a significant initial decrease in SDT and significantly increased OS. MBP loss was abrogated by T cell depletion, neutralization of IFN-γ, and blockade of neutral sphingomyelinase-2. Importantly, when IFN-γ was pulsed onto slices to emulate phasic changes of EE (e.g., activity-rest), significant yet opposite effects were seen: SDT was increased, OS reduced, and MBP elevated above control. The inventors next investigated the involvement of exosomes in these nutritive effects, as exosomes secreted by stressed immune cells can confer protection against OS. Results confirmed that exosomes from IFN-γ-stimulated slice cultures emulated the effects of treatment with phasic low-level IFN-γ. Finally, glutathione, an endogenous sphingomyelinase inhibitor, was significantly increased in microglia, suggesting their involvement in increasing myelin. These results support pulsed application of IFN-γ as a novel therapeutic target for prevention of SD, and by extension, migraine.

EE occurs with physiologically increased neural activity from phasically enhanced learning and memory, and lessened subsequent injury from neurodegenerative disorders including demyelinating diseases. EE promotes T-cell trafficking in the brain (Ziv, et al., 2006), expression of IFN-γ (Pusic, et al., 2010), increases production of myelin (Zhao, et al., 2012), and reduces OS (Radak, et al., 2008). Importantly, enhanced neuronal activity leads to elevated production of antioxidants (Papadia, et al., 2008), including glutathione which inhibits demyelination by blocking sphingomyelinase (Liu et al., 1998), and antioxidants stimulate myelin gene expression (Podratz, et al., 2004).

The inventors probed for further evidence of potentially nutritive effects of IFN-γ/OS-antioxidant interactions on brain myelin using mature hippocampal slice cultures, as T-cells are present and the tissue shows a rise in IFN-γ after SD (Kunkler, et al., 2004). SD is a benign perturbation of brain that is thought to be the most likely cause of migraine aura, and perhaps migraine (Moskowitz, et al., 1993; Lauritzen & Kraig, 2005). When recurrent, SD may also play a role in the conversion of episodic to high frequency and chronic migraine (Kraig et al., 2010). Furthermore, SD increases OS (Grinberg et al., 2012) which may contribute to demyelination, while experimental demyelination promotes SD (Merkler et al., 2009).

Figure 10:
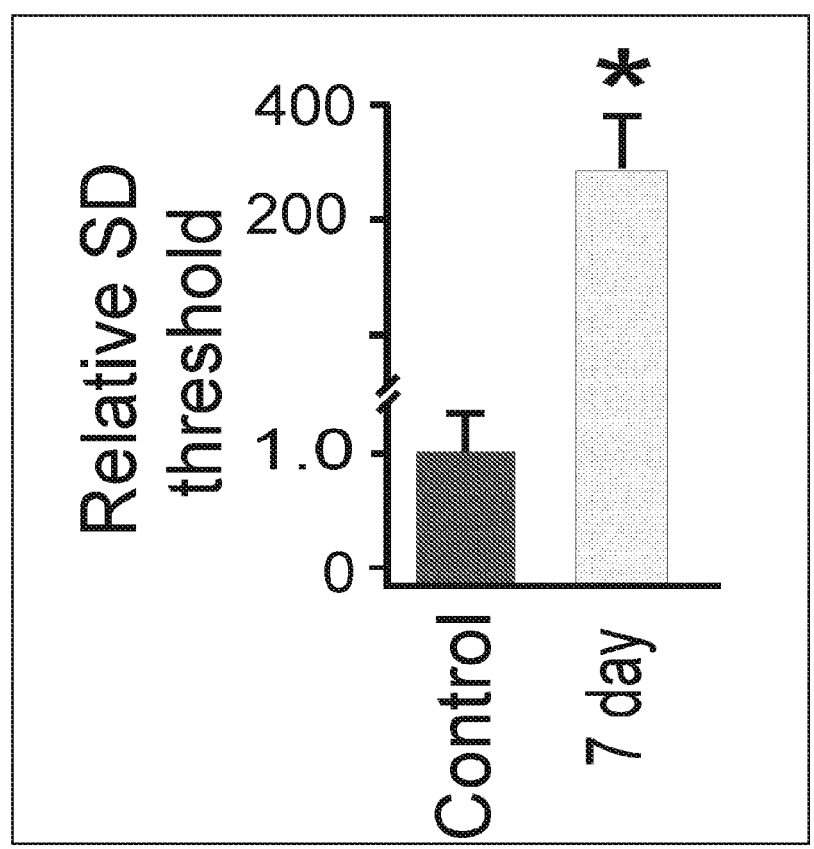
FIG. 10. IFN-γ-stimulated slice cultures released exosomes that mimicked the nutritive effects of pulsed-IFN-γ exposure and reduce susceptibility to spreading depression (SD), the most likely underlying cause of migraine. Immune cells exposed to oxidative stress can secrete exosomes that confer protection against oxidative stress to recipient cells. Likewise, slice cultures stimulated with a 12-hour pulse of IFN-γ released nutritive exosomes that mimicked the positive effects of exposure to pulsed IFN-γ. Slice cultures were exposed to IFN-γ (500 U/mL×12 hours) and returned to normal incubation conditions. Three days later, exosomes were recovered from conditioned media. The latter were applied to naïve slice cultures and measurements made seven days later. IFN-γ-stimulated exosomes triggered a significant a significant (p<0.01), greater than 200-fold increase in SD threshold. Numerical data are mean±SEM and significance (*p<0.05). Comparisons between groups made via paired Student's t-test.

The inventors' results show that SD disrupted the myelin sheath and caused significant but transient loss of MBP that resolved seven days later. Quantitative real-time PCR assay for gene expression analysis revealed mRNA changes consistent with the presence of T cells, a suggestion confirmed by immunostaining for the cells and their production of IFNγ. Continuous application of IFNγ to slices triggered a significant, acute reduction in SD threshold (SDT), increased OS, and reduced MBP. Removal of T cell/IFN-γ and pharmacological blockade of neutral sphingomyelinase-2 abrogated these changes. In contrast, IFNγ applied as a single 12 hour pulse or applied phasically to mimic EE produced opposite, significant effects—MBP increased, SDT increased, and OS was reduced. These effects were also obtained through application of exosomes recovered from IFNγ-stimulated slice culture media, and involved adaptive changes evoked by IFN-γ-induced production of glutathione localized to microglia (FIG. 10).

SD was induced in a static, interface recording configuration as previously described (Pusic et al., 2011; Grinberg et al., 2011; Grinberg et al., 2012). All recording were made at the genu of the CA3 interstitial pyramidal neuron area using 2-4 μm tip diameter micropipettes filled with 150 mM sodium chloride. First, the normalcy of slice electrophysiological behavior was confirmed by monitoring the interstitial field potential responses to bipolar dentate gyrus electrical stimulation (100 μs pulses at ≤0.2 Hz and 5-20 μA). Slices with CA3 field post-synaptic responses≥3 mV were used for experiments. Second, SD threshold was determined by progressively doubling the amount of applied current [10 pulses, 10 Hz (100 μs/pulse)] beginning with that needed to trigger a half-maximal field potential response from a single stimulus. Applied currents for SD threshold were applied no faster than once every 1-3 minutes and they ranged from 10-10,000 nC.

Since stimulated immune cells release exosomes that are capable of reducing OS in recipient cells (Eldh et al., 2010), the inventors searched for involvement of exosomes in generating the nutritive effects of IFN-γ exposure. Slice cultures were exposed to IFN-γ for 12 hours and exosomes harvested from media three days later. They confirmed production and recovery of exosomes from media of IFN-γ stimulated cultures then applied these exosomes to naïve cultures and assessed spreading depression threshold (FIG. 10). Exosomes triggered a significant ($p<0.01$) rise in spreading depression threshold [(n=8/group); Control: 1.00±0.37; Exosomes: 279±94], as well as a significant ($p<0.001$) decrease in OS [measured using CellROX™ after menadione stimulation; Control: 1.00±0.03 (n=6); Exosomes: 0.72±0.02 (n=11)].

Figures 11A, 11B, 11C, 11D, 11E, 11F:
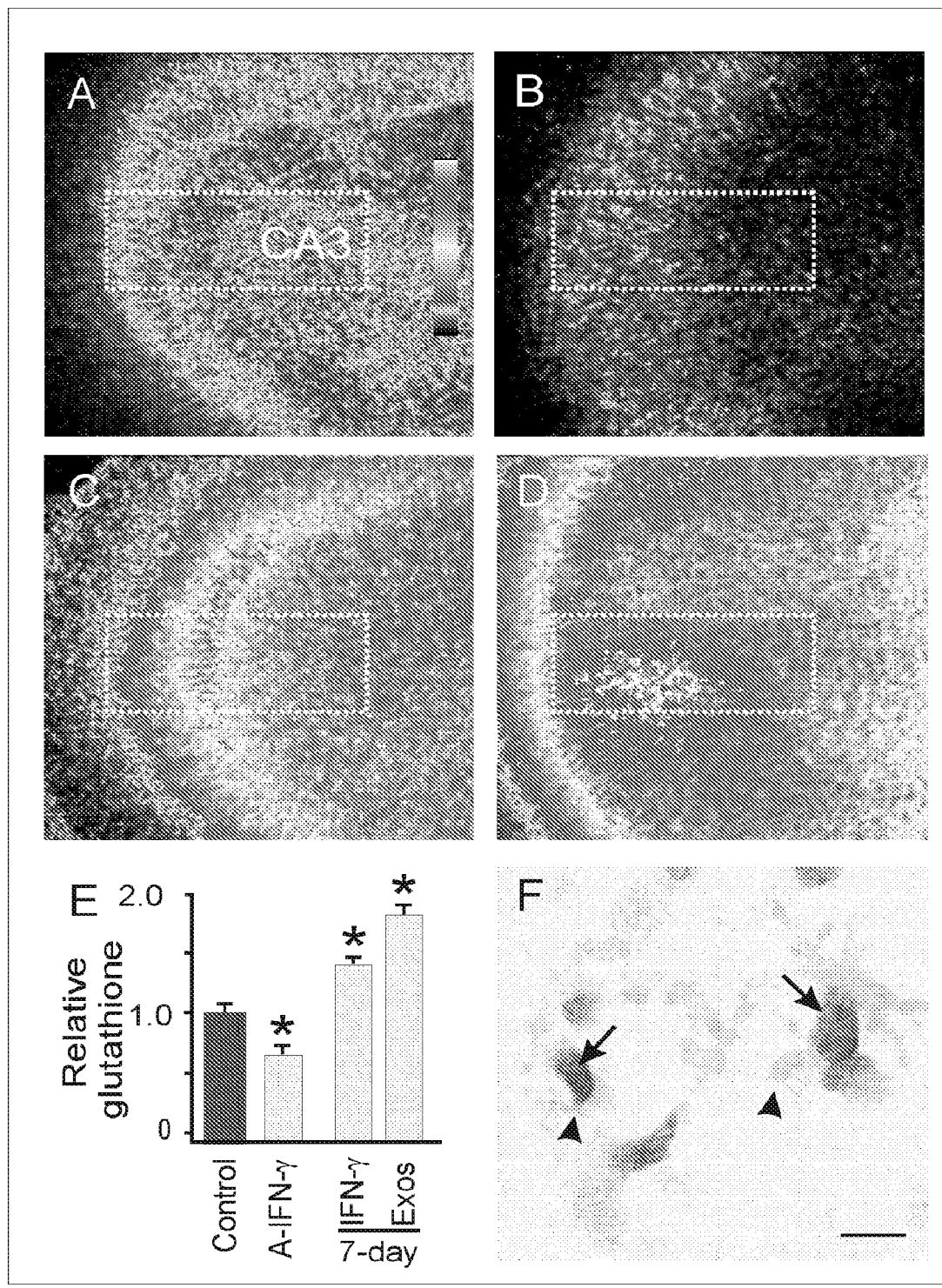
FIGS. 11A-11F. IFN-γ-induced modulation of slice culture glutathione content.
Figures 12A, 12B, 12C:
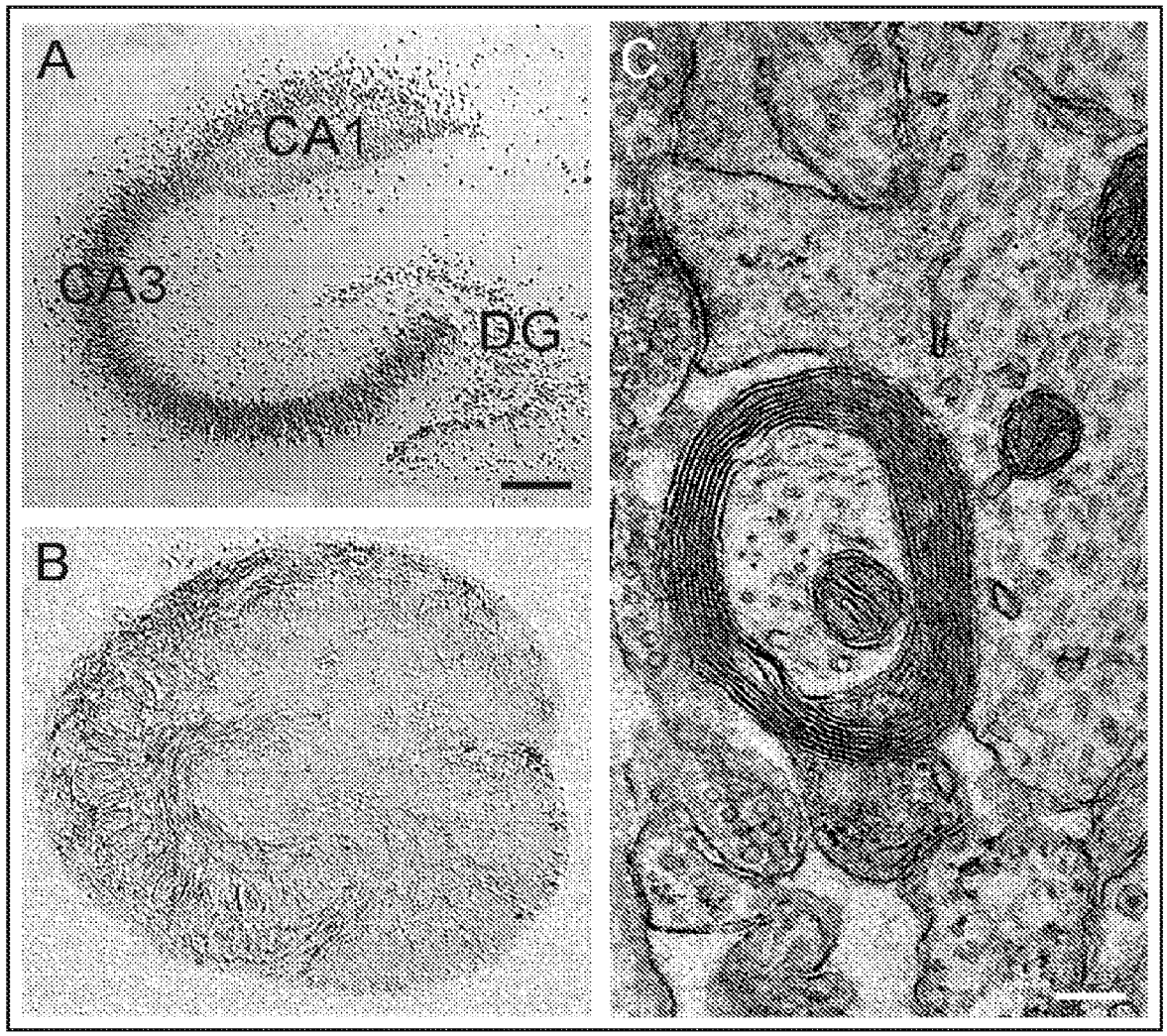
FIGS. 12A-12C. Myelin distribution in hippocampal slice cultures. (A) NeuN staining of hippocampal slice culture illustrates neuronal cytoarchitecture consisting of structurally preserved tri-synaptic loop (dentate gyrus-CA3-CA1). (B) Immunostaining for myelin basic protein shows regional distribution of grey matter myelin in 21 days in vitro hippocampal slice culture that closely parallels that seen in vivo. Scale bar=250 µm. (C) Electron microscopy confirmation of compact myelin in hippocampal slice culture. Exemplary image demonstrates presence of structurally normal, tightly laminated myelin sheath. Scale bar=200 nm.

Exposure to pulsed IFNγ or to exosomes from IFNγ-stimulated cultures both reduced OS. Since the antioxidant glutathione is a naturally occurring inhibitor of neutral sphingomyelinase-2 (Liu et al., 1998), implicated in demyelination, the inventors measured changes in glutathione using Thiol Tracker™ (FIG. 11A-FIG. 11E). Continuous acute IFNγ exposure triggered a significant decline in relative glutathione content, whereas pulsed exposure to IFNγ or exposure to IFNγ-stimulated slice culture exosomes triggered a significant rise in glutathione content at seven-days. Specific values were: Control: 1.00±0.08 (n=21); Acute IFNγ: 0.66±0.07 (n=9); IFNγ: 1.40±0.06 (n=5); Exosomes: 1.82±0.09 (n=6). Cytochemical staining for microglia and confocal imaging confirmed microglia as predominant cell type containing glutathione (FIG. 11F). Thus, T cells/IFNγ stimulated exosomes are a novel therapeutic against high frequency or chronic migraine.

Example 8: Exosome-Mediated Treatment of Traumatic Brain Injury

Traumatic injury to brain is associated with loss of oligodendrocytes, the myelin producing cells of the brain, demyelination, and a failure of inured brain areas to adequately remyelinate (Flygt, et al., 2013). However, new evidence indicates that injured brain may be able to remyelinate if adequately stimulated (Powers, et al., 2013).

Experimental work from the inventors indicates that exosomes can be a novel therapeutic for recovery from traumatic brain injury. This conclusion follows from the following facts. Spreading depression (SD) worsens clinical outcome from traumatic brain injury (Hartings, et al., 2011) and the inventors have shown that exosomes can significantly prevent SD.

For example, exosomes derived from the serum of rats exposed to environmental enrichment (EE) for four-eight weeks produce exosomes that reduce susceptibility to SD after application to hippocampal slice cultures for three days. EE-exosome application significantly ($p=0.006$) reduced SD susceptibility compared to control with specific values of: EE-Exo treated cultures: 304±88 versus control: 1.00±0.35 (n=6/group).

In addition, application of IFNγ-stimulated dendritic cell exosomes to slice cultures for three days also produced a significant ($p<0.001$) reduction in spreading depression susceptibility compared to control. Specific values were: IFNγ-dendritic cell exosome treated slices: 12.5±1.52 versus control: 1.00±0.45 (n=8/group).

Example 9: Exosome-Mediated Treatment of Neonatal Brain Injury

Neonatal brain injury commonly results in injury to oligodendrocytes with associated hypomyelination (Kauer & Ling EA, 2009). Since exosomes derived from the serum of environmentally enriched animals as well as those derived from IFNγ-stimulated dendritic cells in vitro, promote oligodendrocyte differentiation and related myelin production, the inventors determined the impact of these potential therapeutic agents on neonatal ischemic brain injury.

Experiments were performed in developing hippocampal slice cultures. The slice cultures were prepared as previously described (Mitchell, et al., 2010) using P9-P10 rat pups, except that cultures were transferred to serum-free media after four days in vitro. This was done to prevent any confounding effects of exosomes from horse-serum, that is otherwise an early media constituent.

At the same time, cultures were exposed to oxygen-glucose deprivation (OGD; Markus, et al., 2009) to model neonatal ischemic brain injury.

After OGD, cultures were treated with exosomes derived from IFNγ-stimulated dendritic cells grown in vitro, then allowed to mature until 21 days in vitro (i.e., consistent with P31 rats). Cultures were then harvested for measurement of myelin basic protein (MBP) via Western blot.

Exosome treatment resulted in a significant ($p=0.002$) improvement of MBP levels post OGD exposure. Specific values were: control: 1.00±0.20; OGD treated cultures: 0.40±0.03; and OGD+IFNγ-stimulated dendritic cell exosomes: 1.37±0.17 (n 6/group).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ahlskog, et al., *May Clin Proc.* 86:876-884, 2011.
Alam and Cook, 1990
Birgbauer, et al., *J Neurosci Res,* 2004.
Bobrie, et al., *Traffic* 12:1665-1668, 2011.
Costa et al., 2001.
Dubey et al., 2003.
Eldh et al. *PLoS ONE* 5(12): e15353, 2010.
Fancy et al., *Nature Neuroscience* 14, 1009-1016, 2011.
Flygt, et al., *Eur J Neurosci,* 2013.
Gallagher et al., *ILAR J* 8:52:32-40, 2011.
Gobbo & O'Mara, *Behav Brain Res* 152:231-241, 2004.
Grinberg et al., *PLoS One* 6:e19294, 2011.
Grinberg et al., *J Neurochem* 122:221-229, 2012.
Grinberg et al., *PLoS ONE,* 2011.
Grinberg, et al. *J Neurochem.* 122:221-9, 2012.
Hartings, et al., *Brain,* 2011.
Johnson et al., *Experimental Neurology,* 246:35-43, 2013.
Johnstone, et al., *J Biol Chem.* 262:9412-9420, 1987.
Kauer & Ling, *Prog Neurobiol,* 2009.
Kochnc et al. (2003.
Kraig et al., *Dose Response* 8:389-413, 2010.
Kumar, 2005.
Kundra et al., 2002.
Kundra et al., 2005.
Kunkler et al., *Soc Neurosci* 32:Prog#87.5, 2004.
Kunkler et al., *Soc Neurosci,* 2006.
Lauritzen & Kraig, *Metab Brain Dis* 7:157-164, 2005.
Lee, et al., *Semin Immunopathol* 33:455-467, 2011.
Lin et al., *Am J Pathol,* 2008.
Linchey and Fridovich, 1997.
Liu et al., *J Biol Chem* 273:11313-20, 1998.
Markus et al., *J Cereb Blood Flow & Met,* 29(1):73-86, 2009.
Merkler et al., *Ann Neurol* 66:355-365, 2009.
Mitchell, et al., *JoVE,* 43:2010.
Mitchell, et al., *J Neurochem.* 117:187-196, 2011.
Moskowitz et al., *J Neurosci.* 13:1167-1177, 1993.
Obiang, et al. *Neurobiol Learn Mem.* 96:121-129, 2011.
Papadia et al., *Nat Neurosci* 11:476-487, 2008.
Podratz et al., *Glia.* 45:54-58, 2004.
Powers, et al., *PNAS,* 110(11):4075-80, 2013.
Pusic, et al., *Soc Neurosci.* 36: Prog #346.2, 2010.
Pusic, et al., *J Vis Exp.* 52, 2011.
Pusic, et al., *J Vis Exp.* doi: 10.3791/2910, 2011.
Radak et al., *Free Radic Biol Med.* 44:153-159, 2008.
Raposo, et al., *J Exp Med* 183:1161-1172, 1996.
Ruckh, et al., *Cell Stem Cell,* 10(1):96-103, 2012.
Sanchez, et al., *Proc Natl Acad Sci USA.* 106:9848-9853, 2009.
Schorey & Bhatnagar, *Traffic.* 9:871-881, 2008.
Skog, et al., *Nat Cell Biol.* 10:1470-1476, 2008.
Sohal & Weindruch, *Science.* 5:59-63, 1996.
Suresh et al., 1993.
Valadi, et al., *Nat Cell Biol.* 9:654-659, 2007.
Wheeler et al., 2001.
WO99/03499
WO00/44389
WO01/82958
Zhao, et al., *Anat Rec,* 6:999-1005, 2012.
Zhuang, et al., *Mol Ther.* 19(10):1769-79, 2011.
Ziv, et al., *Nat Neurosci* 9:268-275, 2006.

The invention claimed is:

1. A method for treating a patient having a demyelinating disorder comprising administering to the patient an effective amount of a pharmaceutical composition comprising isolated exosomes obtained from cells that have been incubated with IFN-γ, wherein the cells are microglia, T cells, B cells, dendritic cells, or peripheral blood mononuclear cells.

2. The method of claim 1, wherein the cells are microglia.

3. The method of claim 1, wherein the cells are T cells, B cells, or dendritic cells.

4. The method of claim 1, wherein the cells are peripheral blood mononuclear cells.

5. The method of claim 1, wherein the cells are obtained from the patient.

6. The method of claim 1, wherein the demyelinating disorder is cognitive decline, Alzheimer's disease, Parkinson's disease, stroke, epilepsy, migraine, multiple sclerosis, traumatic brain injury, or neuropathy.

7. The method of claim 6, wherein the demyelinating disorder is multiple sclerosis.

8. The method of claim 1, wherein the isolated exosomes comprise miR-219, miR-138, or miR-199a.

9. The method of claim 1, wherein the administering step causes growth or repair of myelin in the patient.

10. The method of claim 1, wherein the isolated exosomes are enriched for miRNAs that promote oligodendrocyte differentiation.

11. A method for treating a patient having a demyelinating disorder comprising:
(a) adding IFN-γ to cells and incubating the cells in the presence of the added IFN-γ, wherein the cells comprise microglia, T cells, B cells, dendritic cells, or peripheral blood mononuclear cells;
(b) harvesting exosomes produced by the cells; and
(c) administering to the patient an effective amount of a pharmaceutical composition comprising the exosomes.

12. The method of claim 11, further comprising obtaining the cells from the patient before step (a).

13. The method of claim 11, wherein the cells are dendritic cells.

14. The method of claim 11, wherein the cells are T cells or B cells.

15. The method of claim 11, wherein the cells are peripheral blood mononuclear cells.

16. The method of claim 11, wherein the cells are microglia.

17. The method of claim 11, wherein the demyelinating disorder is cognitive decline, Alzheimer's disease, Parkinson's disease, stroke, epilepsy, migraine, multiple sclerosis, traumatic brain injury, or neuropathy.

18. The method of claim 17, wherein the demyelinating disorder is multiple sclerosis.

19. The method of claim 1, wherein the demyelinating disorder is migraine.

20. The method of claim 17, wherein the demyelinating disorder is migraine.

* * * * *

UNITED STATES PATENT AND TRADEMARK OFFICE
CERTIFICATE OF CORRECTION

| | |
|---|---|
| PATENT NO. | : 11,369,634 B2 |
| APPLICATION NO. | : 16/259563 |
| DATED | : June 28, 2022 |
| INVENTOR(S) | : Pusic et al. |

It is certified that error appears in the above-identified patent and that said Letters Patent is hereby corrected as shown below:

In the Claims

On Column 44, Line 39 should read as follows:
(a) adding IFN-γ to cells and incubating the cells in the Signed and Sealed this
Twelfth Day of September, 2023

Katherine Kelly Vidal
*Director of the United States Patent and Trademark Office*